United States Patent
Yen

(10) Patent No.: US 9,537,103 B1
(45) Date of Patent: Jan. 3, 2017

(54) MATERIAL FOR ORGANIC ELECTROLUMINESCENCE DEVICE AND ORGANIC ELECTROLUMINESCENCE DEVICE USING THE SAME

(71) Applicant: LUMINESCENCE TECHNOLOGY CORPORATION, Hsin-Chu (TW)

(72) Inventor: Feng-Wen Yen, Taipei (TW)

( * ) Notice: Subject to any disclaimer, the term of this patent is extended or adjusted under 35 U.S.C. 154(b) by 0 days.

(21) Appl. No.: 14/826,211

(22) Filed: Aug. 14, 2015

(51) Int. Cl.
*H01L 51/00* (2006.01)
*C07C 211/61* (2006.01)
(Continued)

(52) U.S. Cl.
CPC .......... *H01L 51/0056* (2013.01); *C07C 13/62* (2013.01); *C07C 211/61* (2013.01); *C07D 209/86* (2013.01); *C07D 239/26* (2013.01); *C07D 251/24* (2013.01); *C07D 307/91* (2013.01); *C07D 333/76* (2013.01); *C07D 471/04* (2013.01); *C09K 11/02* (2013.01); *C09K 11/025* (2013.01); *C09K 11/06* (2013.01); *H01L 51/006* (2013.01); *H01L 51/0058* (2013.01); *H01L 51/0061* (2013.01); *H01L 51/0067* (2013.01); *H01L 51/0072* (2013.01); *H01L 51/0074* (2013.01); *C07C 2103/24* (2013.01); *C07C 2103/54* (2013.01); *C07C 2103/97* (2013.01); *C09K 2211/1007* (2013.01); *C09K 2211/1011* (2013.01); *C09K 2211/1014* (2013.01); *C09K 2211/1022* (2013.01);
(Continued)

(58) Field of Classification Search
CPC ........ H01L 51/0032–51/0095; H01L 27/32–27/3297
See application file for complete search history.

(56) References Cited

U.S. PATENT DOCUMENTS 8,962,160 B2   2/2015   Yen et al.
8,993,130 B2   3/2015   Yen et al.
(Continued)

FOREIGN PATENT DOCUMENTS

WO   2008062636 A1   5/2008
WO   2012091471 A2   7/2012

*Primary Examiner* — Mamadou Diallo

(57) ABSTRACT

The present invention discloses an organic material is represented by the following formula(A), the organic EL device employing the material as light emitting host or dopant of emitting layer, hole blocking layer(HBL), electron blocking layer(EBL), electron transport layer(ETL) and hole transport layer (HTL) can display good performance.

formula (A)

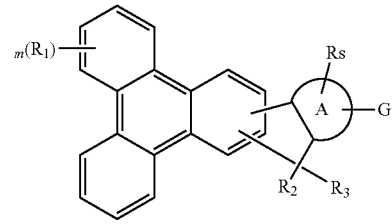

wherein A represents a substituted or unsubstituted fused ring hydrocarbon units with two to three rings, m represents an integer of 0 to 10, G, Rs and $R_1$ to $R_3$ are the same definition as described in the present invention.

18 Claims, 3 Drawing Sheets

| 14 | — metal electrode |
| 13 | — electron injection layer |
| 12 | — electron transport layer |
| 11 | — hole blocking layer |
| 10 | — emitting layer |
| 9  | — electron blocking layer |
| 8  | — hole transport layer |
| 7  | — hole injection layer |
| 6  | — transparent electrode |

(51) Int. Cl.
| | |
|---|---|
| *C07D 307/91* | (2006.01) |
| *C07D 471/04* | (2006.01) |
| *C07D 251/24* | (2006.01) |
| *C07D 239/26* | (2006.01) |
| *C07D 333/76* | (2006.01) |
| *C07D 209/86* | (2006.01) |
| *C09K 11/02* | (2006.01) |
| *C09K 11/06* | (2006.01) |
| *C07C 13/62* | (2006.01) |
| *H01L 51/50* | (2006.01) |

(52) U.S. Cl.
CPC ............. *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0073* (2013.01); *H01L 51/5012* (2013.01); *H01L 51/5036* (2013.01); *H01L 51/5056* (2013.01); *H01L 51/5072* (2013.01); *H01L 51/5096* (2013.01)

(56) References Cited

U.S. PATENT DOCUMENTS

| | | | |
|---|---|---|---|
| 2013/0048975 A1 | 2/2013 | Hong et al. | |
| 2014/0131664 A1* | 5/2014 | Yen | C07C 13/62 257/40 |
| 2014/0151645 A1 | 6/2014 | Yen et al. | |
| 2014/0166988 A1* | 6/2014 | Yen | H01L 51/0058 257/40 |
| 2014/0175383 A1 | 6/2014 | Yen et al. | |
| 2014/0209866 A1 | 7/2014 | Yen | |
| 2014/0231754 A1 | 8/2014 | Yen et al. | |
| 2014/0306214 A1* | 10/2014 | Lee | H01L 51/5228 257/40 |
| 2016/0218292 A1* | 7/2016 | Yen | H01L 51/0056 |

* cited by examiner

MATERIAL FOR ORGANIC ELECTROLUMINESCENCE DEVICE AND ORGANIC ELECTROLUMINESCENCE DEVICE USING THE SAME

FIELD OF INVENTION

The present invention generally relates to a material and organic electroluminescence(herein referred to as organic EL) device using the material. More specifically, the present invention relates to the material having general formula(A), an organic EL device employing the material as emitting host or dopant, hole blocking layer(HBL), electron blocking layer(EBL), electron transport layer(ETL) and hole transport layer(HTL).

BACKGROUND OF THE INVENTION

Organic electroluminescence(organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current(DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer(HTL), an emitting layer (EML) and an electron transporting layer(ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO(lowest unoccupied molecular orbital) and holes will be injected from an anode into a HOMO(highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT(metal to ligand charge transfer) state of organic metallic complexes.

Recently, a new type of fluorescent organic EL incorporating mechanism of thermally activated delayed fluorescence(TADF) has been developed by Adachi and coworkers is a promising way to obtain a high efficiency of exciton formation by converting spin-forbidden triplet excitons up to the singlet level by the mechanism of reverse intersystem crossing(RISC).

The phosphorescent organic EL utilizes both triplet and singlet excitons. Cause of longer lifetime and the diffusion length of triplet excitons compared to those of singlet excitons, the phosphorescent organic EL generally need an additional hole-blocking layer(HBL) between the emitting layer(EML) and the electron transporting layer(ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO(highest occupied molecular orbital)and LUMO(lowest unoccupied molecular orbital) energy levels suitable to block hole transport from the EML to the ETL and to pass electrons from the ETL to the EML, in addition, the good thermal and electrochemical stability of the materials are also needed.

There continues to be a need for organic EL materials which is able to efficiently transport electrons or holes and block holes, with good thermal stability and more efficient EML materials for high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel material having general formula(I), used as emitting host or dopant, hole blocking layer(HBL), electron blocking layer(EBL), electron transport layer(ETL) and hole transport layer(HTL) have good charge carrier mobility and excellent operational durability can lower driving voltage and power consumption, increasing efficiency and half-life time of organic EL device.

SUMMARY OF THE INVENTION

A novel material can use as emitting host or dopant, hole blocking layer(HBL), electron blocking layer(EBL), electron transport layer(ETL) and hole transport layer(HTL) for organic EL and their use for organic EL device are provided. The material can overcome the drawbacks of the conventional materials like as shorter half-life time, lower efficiency and higher power consumption.

An object of the present invention is to provide the material which can be used as hole blocking layer(HBL) material, electron blocking layer(EBL) material for organic EL device and can efficiently confine excitons to transfer to electron transport layer or hole transport layer.

An object of the present invention is to provide the material which can be used as phosphorescent host material, fluorescent host material or fluorescent dopant of emitting layer for organic EL device and increase the efficiency and half-life time.

Another object of the present invention is to provide the material which can be used as hole transport layer(HTL) material, electron transport layer(ETL) material for organic EL device and improve the half-life time, lower driving voltage and lower power consumption.

The present invention has the economic advantages for industrial practice. Accordingly the present invention, the material which can be used for organic EL device is disclosed. The mentioned the material is represented by the following formula(A):

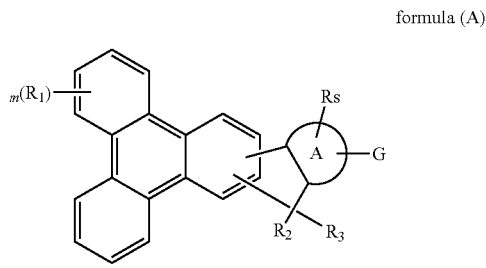

formula (A)

wherein A represents a substituted or unsubstituted fused ring hydrocarbon units with two to three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $R_s$ represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

DESCRIPTION OF THE PREFERRED EMBODIMENTS

Figure 1:
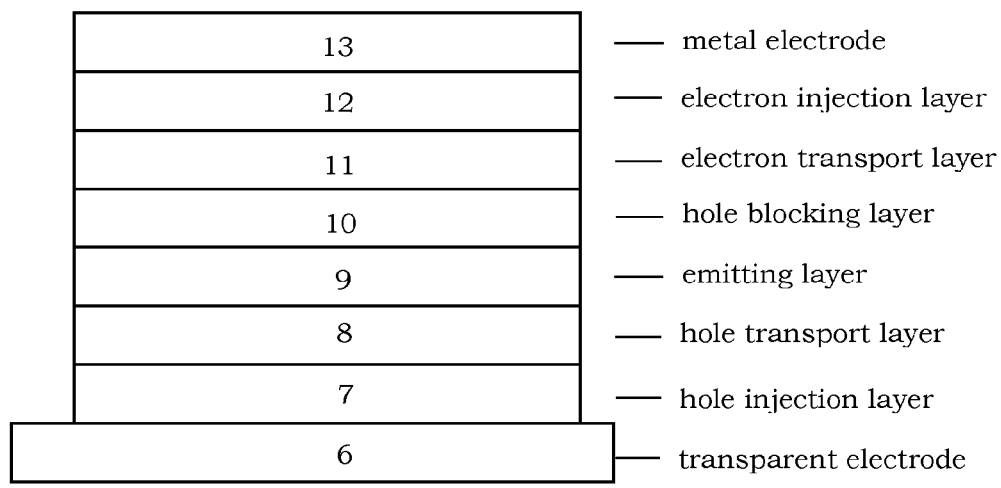
FIG. 1 show one example of organic EL device in the present invention. 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

What probed into the invention is the material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the material which can be used as emitting host or dopant, hole blocking layer(HBL), electron blocking layer(EBL), electron transport layer(ETL) and hole transport layer(HTL) for organic EL device are disclosed. The mentioned the material are represented by the following formula(A):

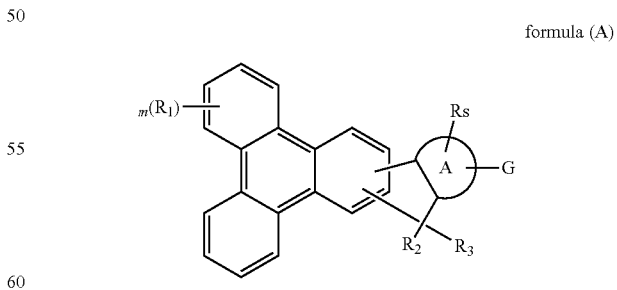

formula (A)

wherein A represents a substituted or unsubstituted fused ring hydrocarbon units with two to three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $R_s$ represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

According to the above-mentioned the material formula (A), wherein the G is consisting of group represented as follows:

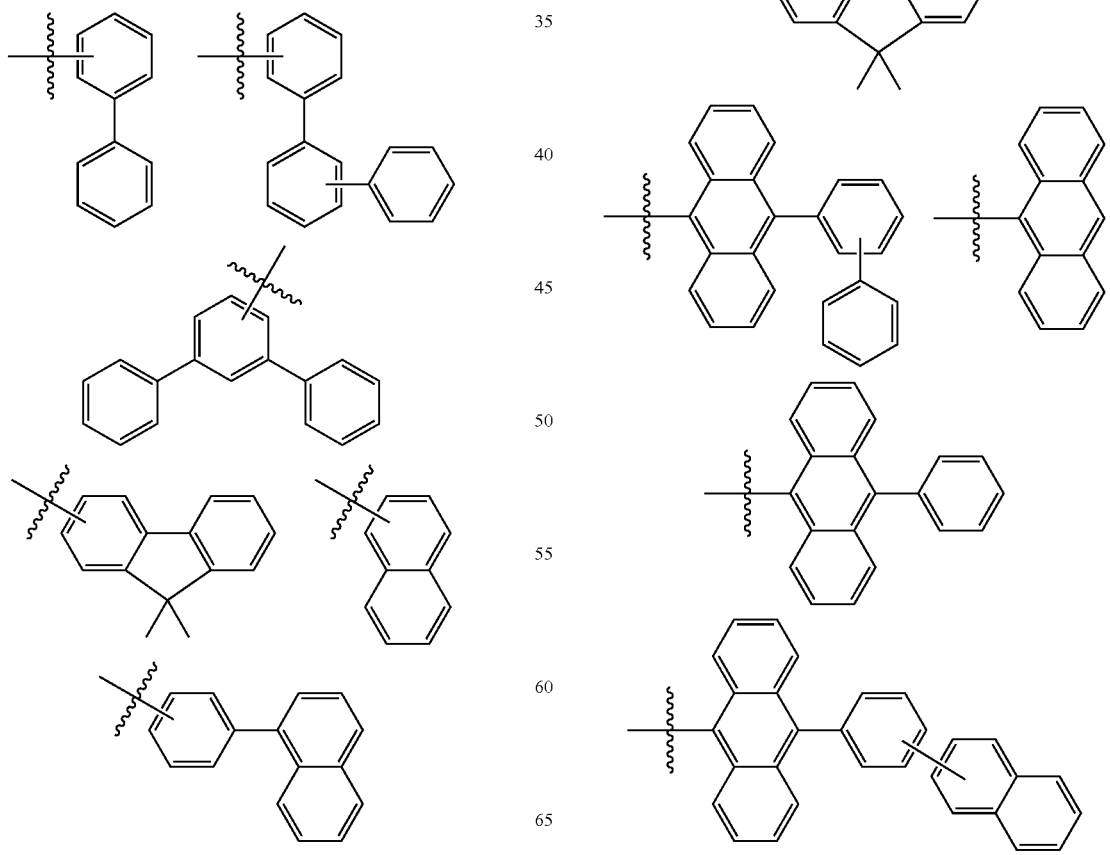

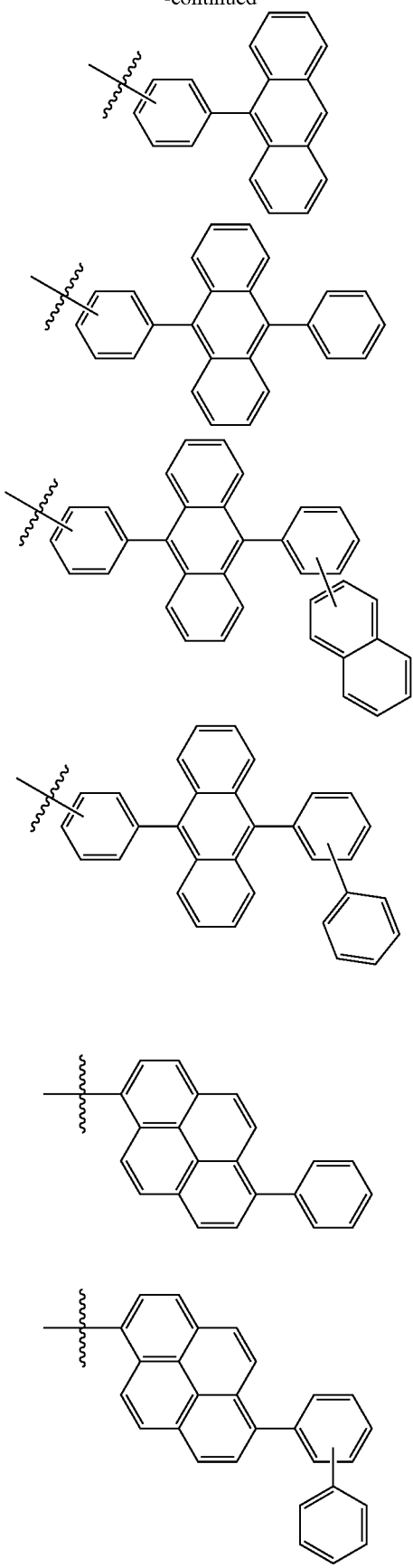
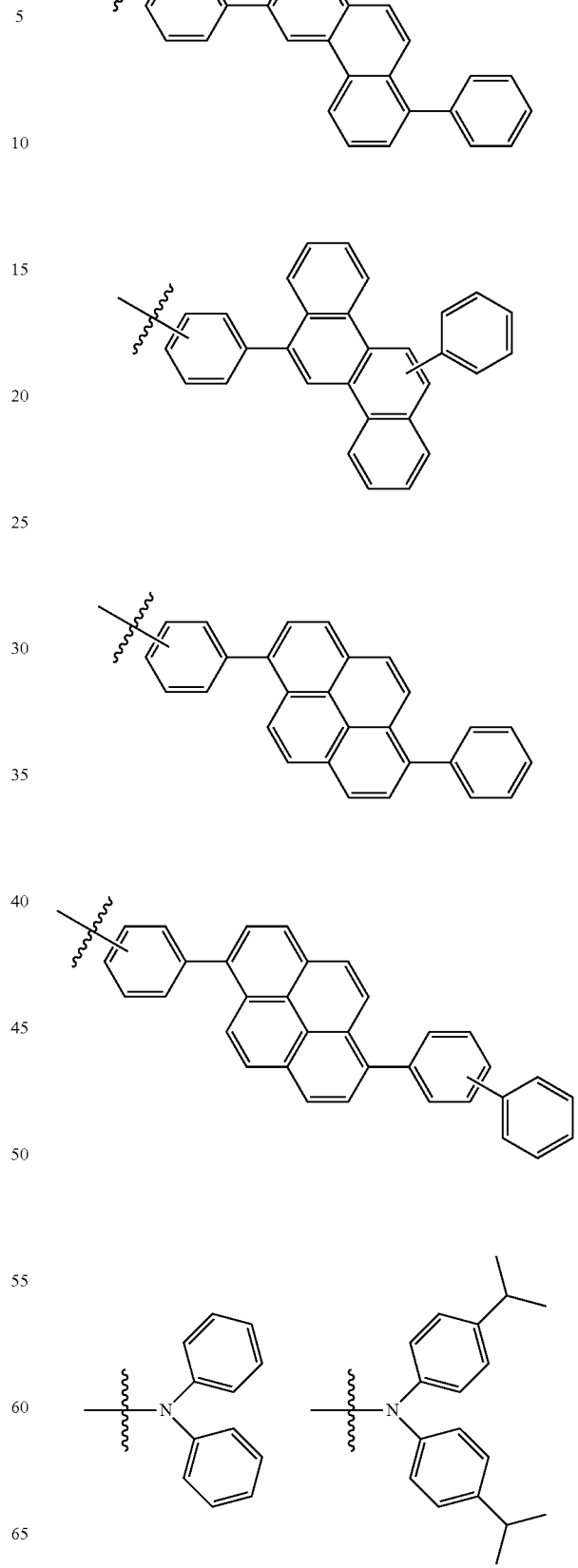

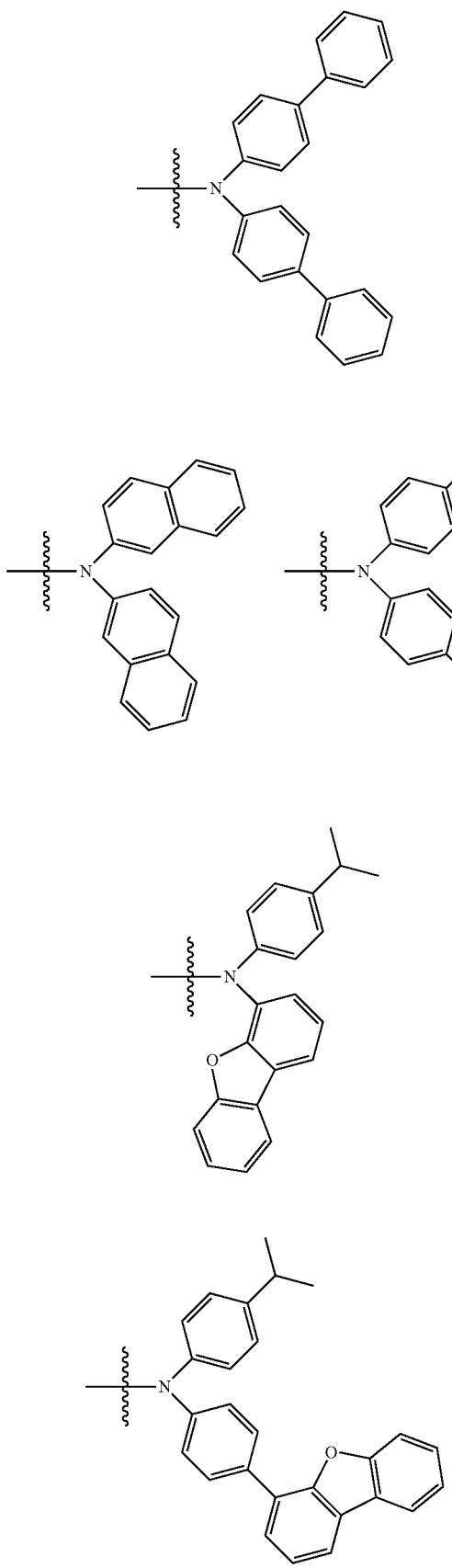
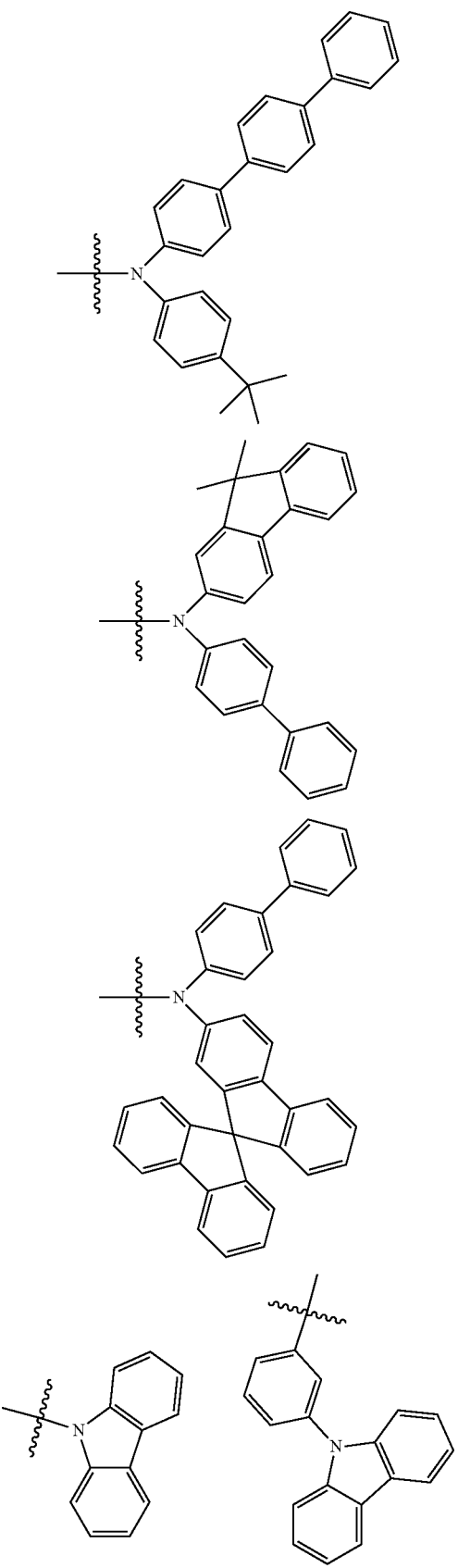

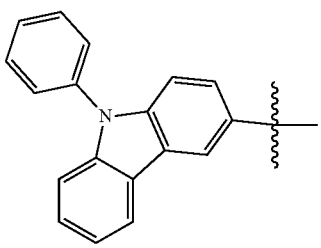
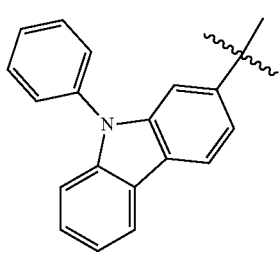
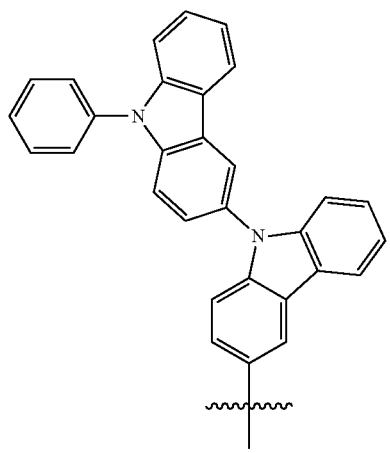
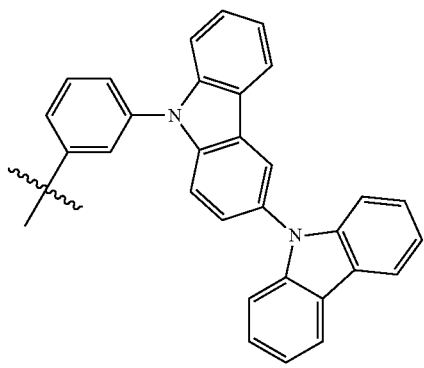
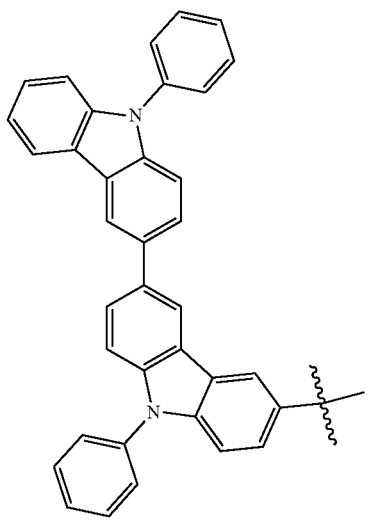
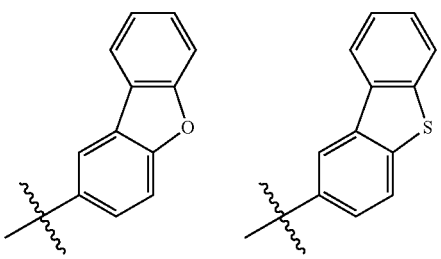
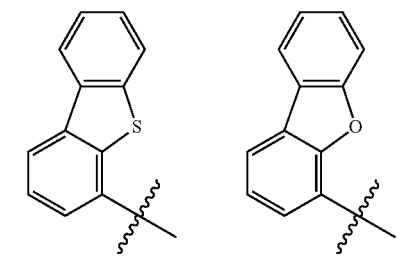
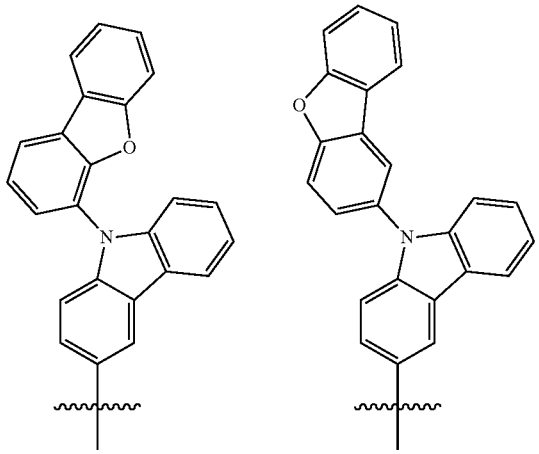

-continued
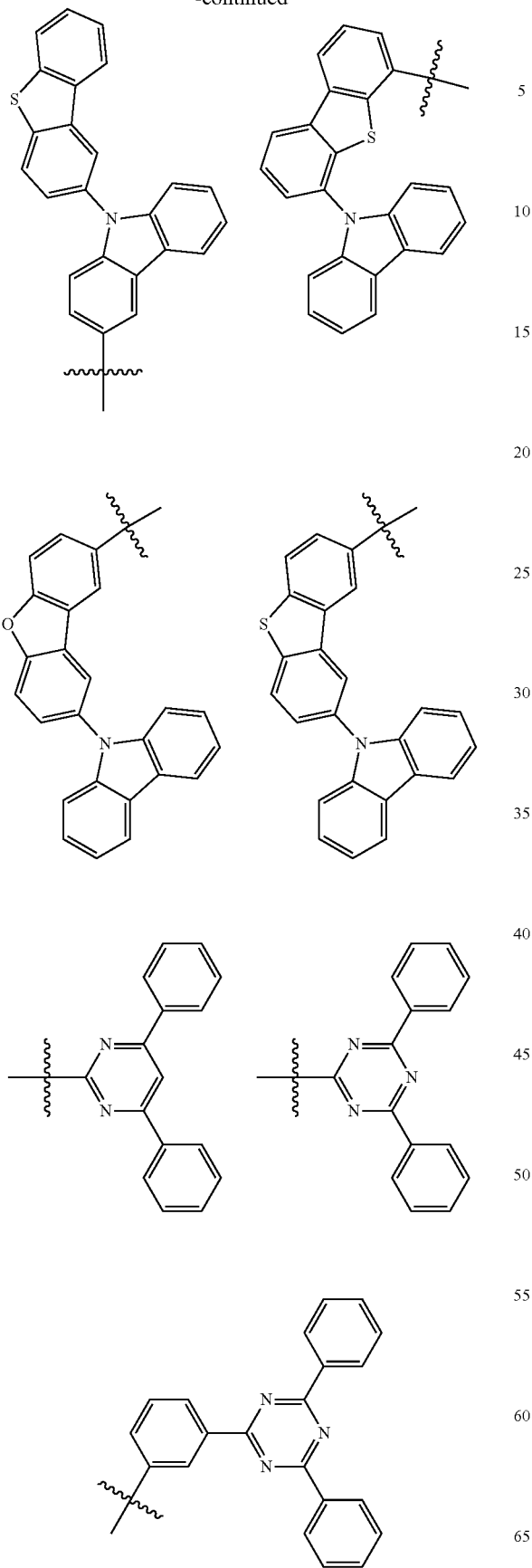
-continued

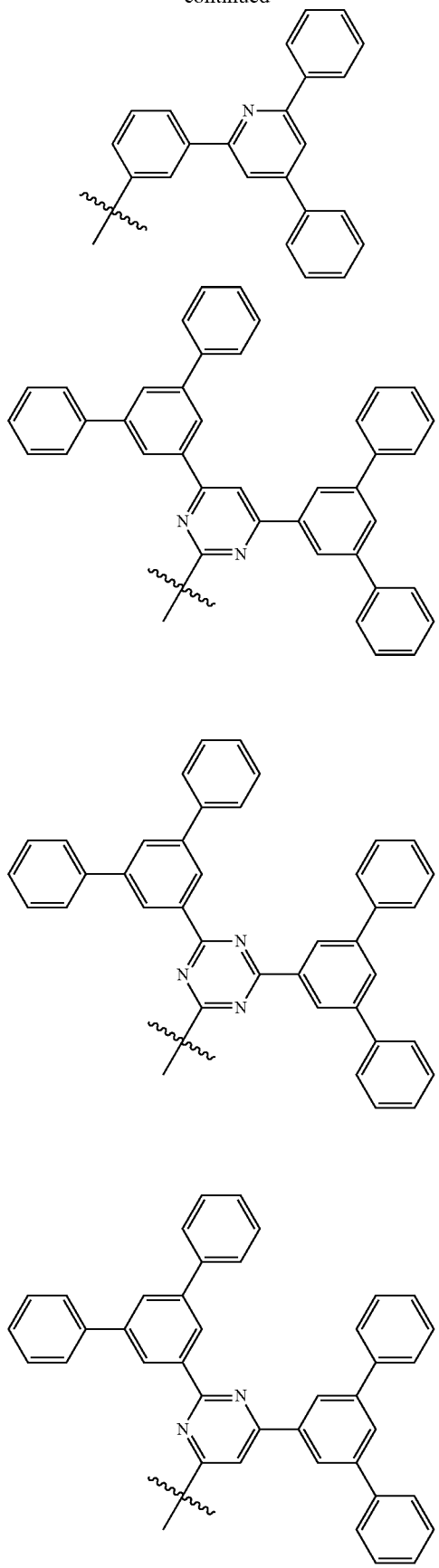
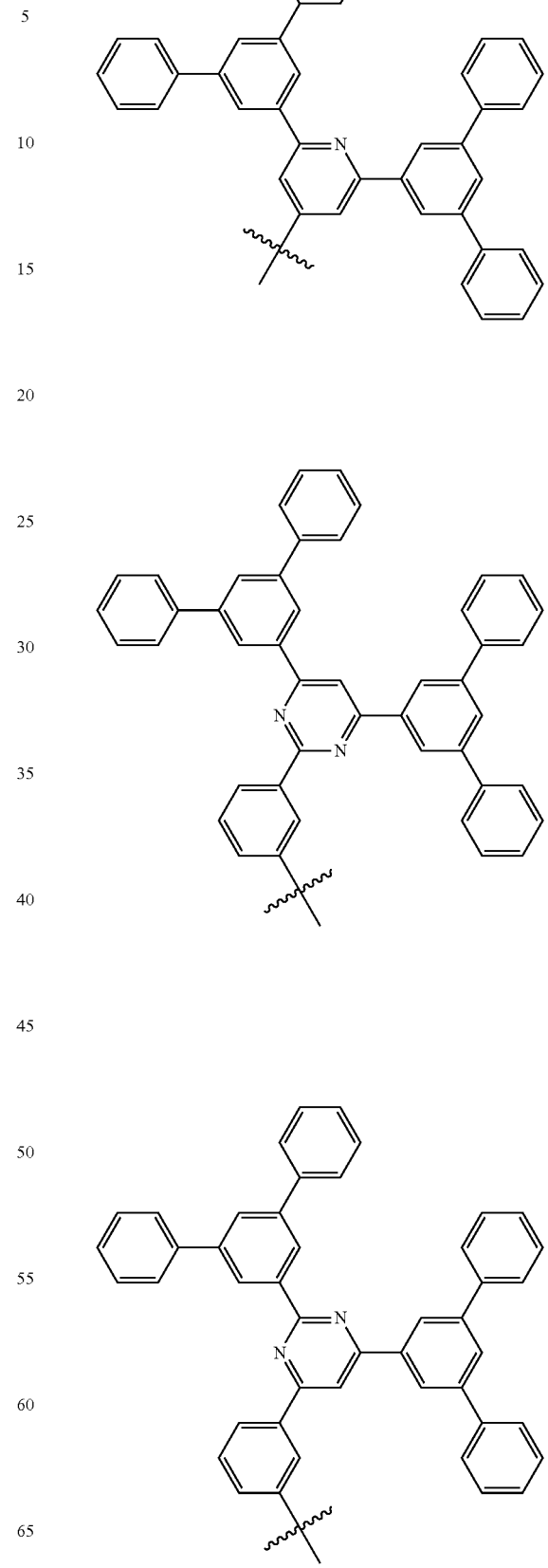

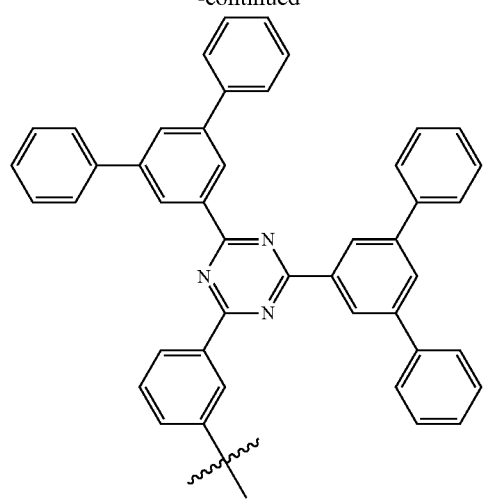
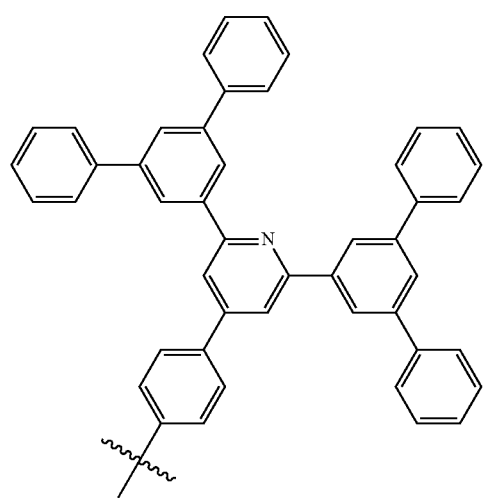
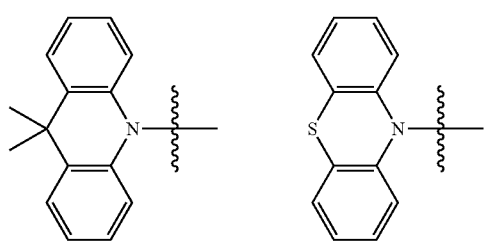
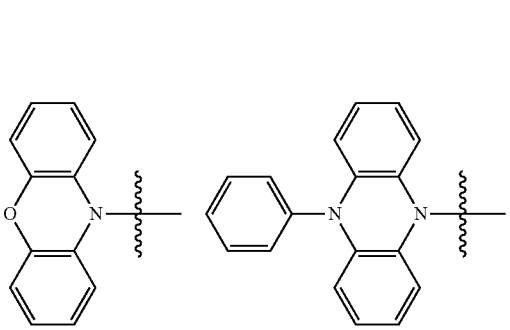
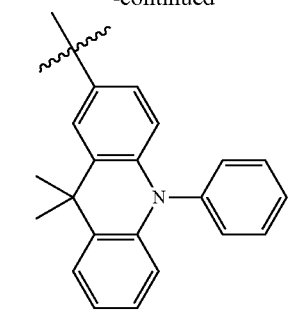
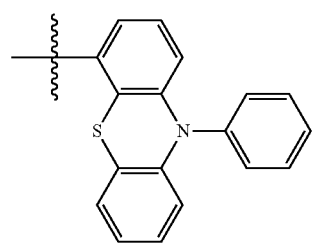
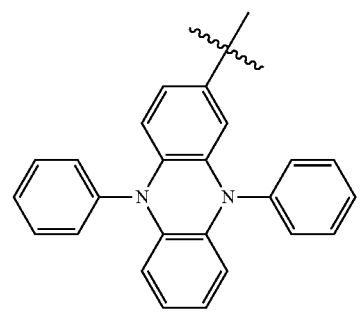
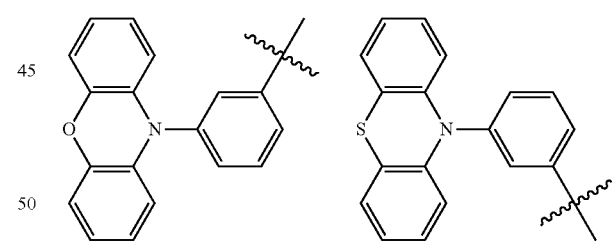
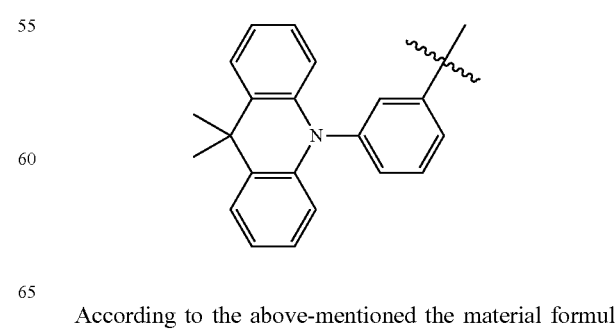
According to the above-mentioned the material formula (A) represented by the following formula(1) to formula(9):

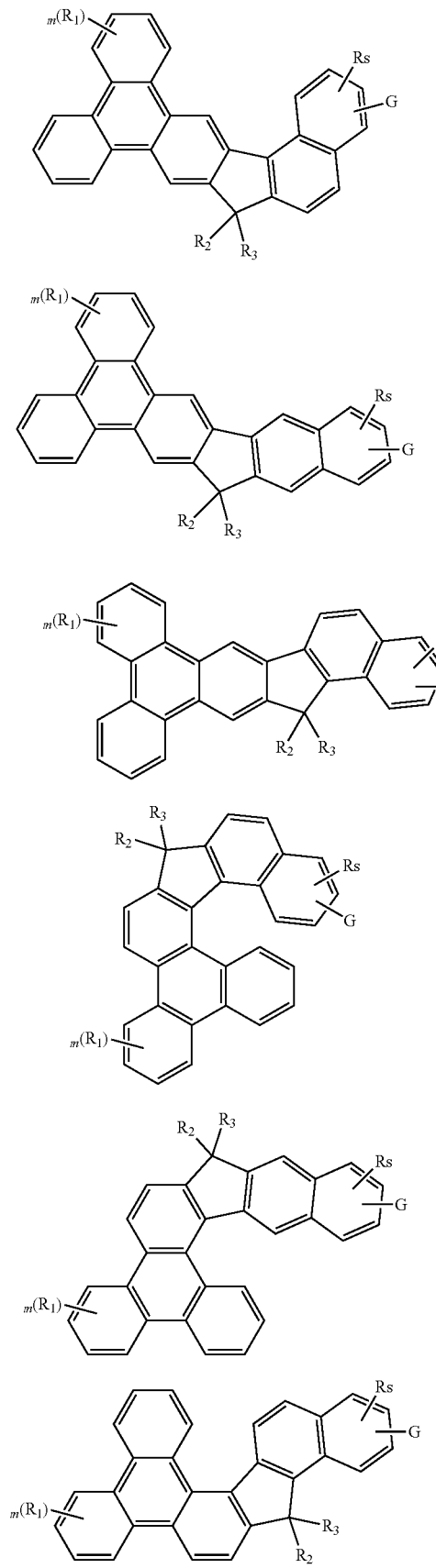

formula(1)
formula(2)
formula(3)
formula(4)
formula(5)
formula(6)
formula(7)
formula(8)
formula(9)

wherein m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and G preferably represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $R_s$ represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

According to the above-mentioned the material formula (1) to formula(9) wherein the G is consisting of group represented as follows:

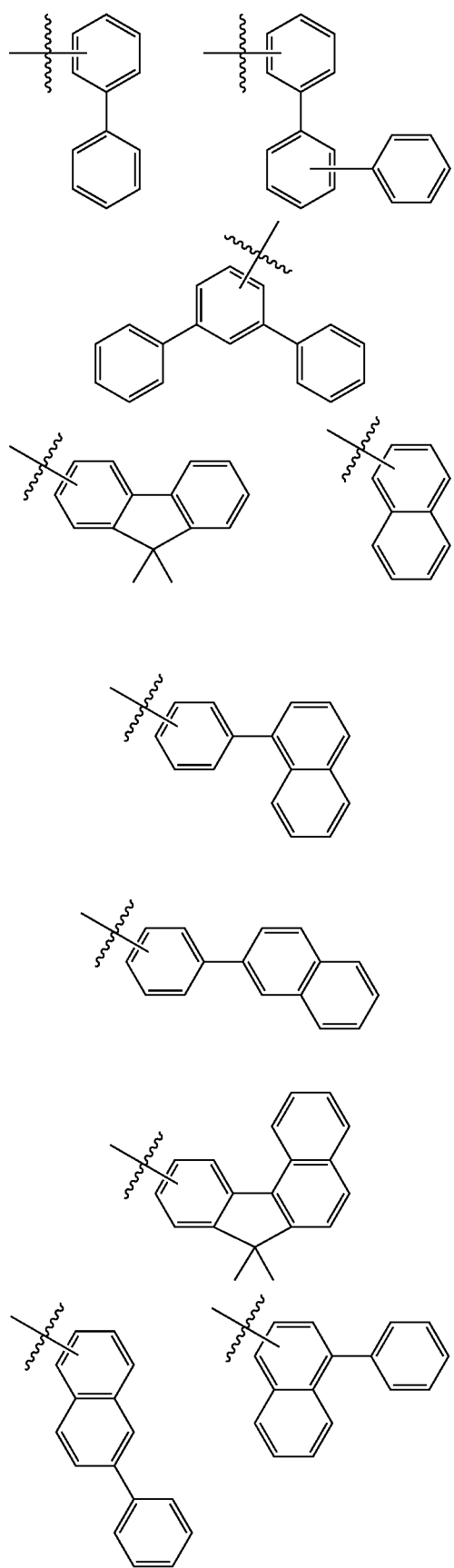
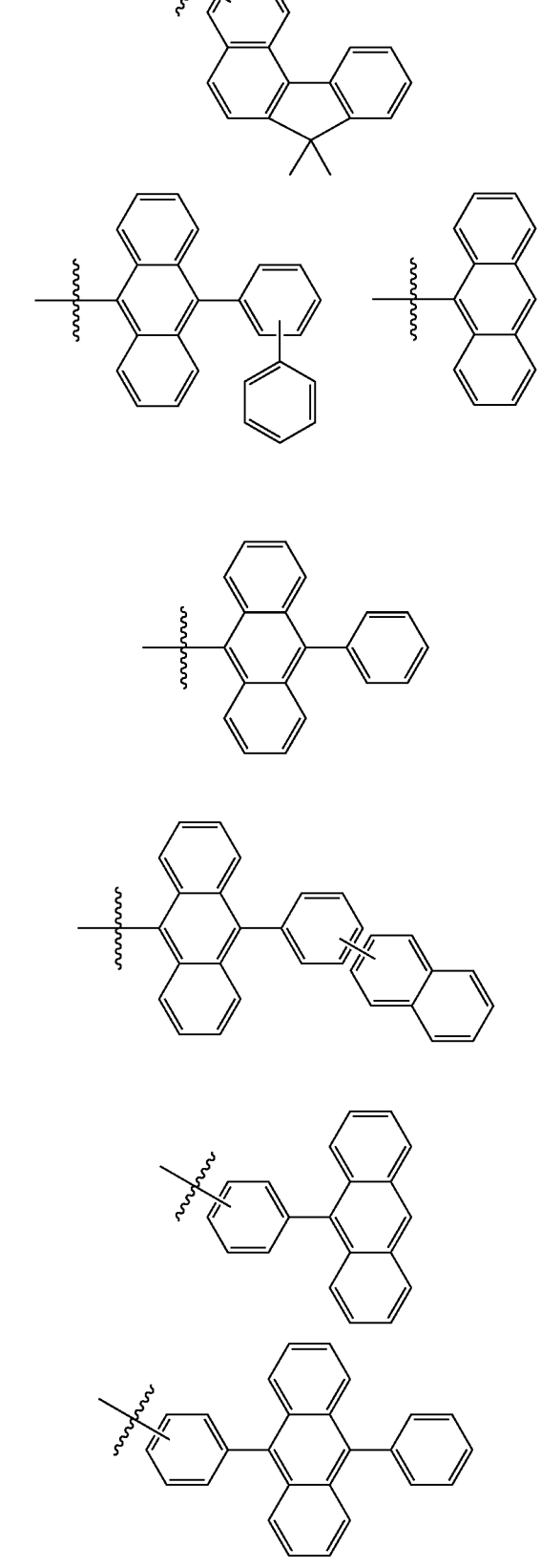
-continued

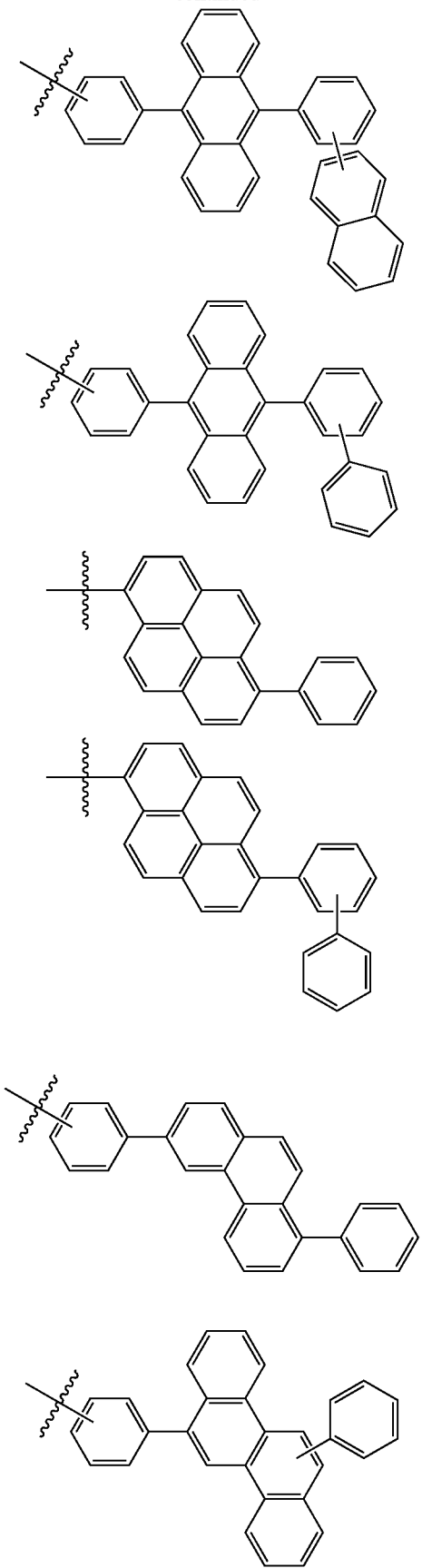
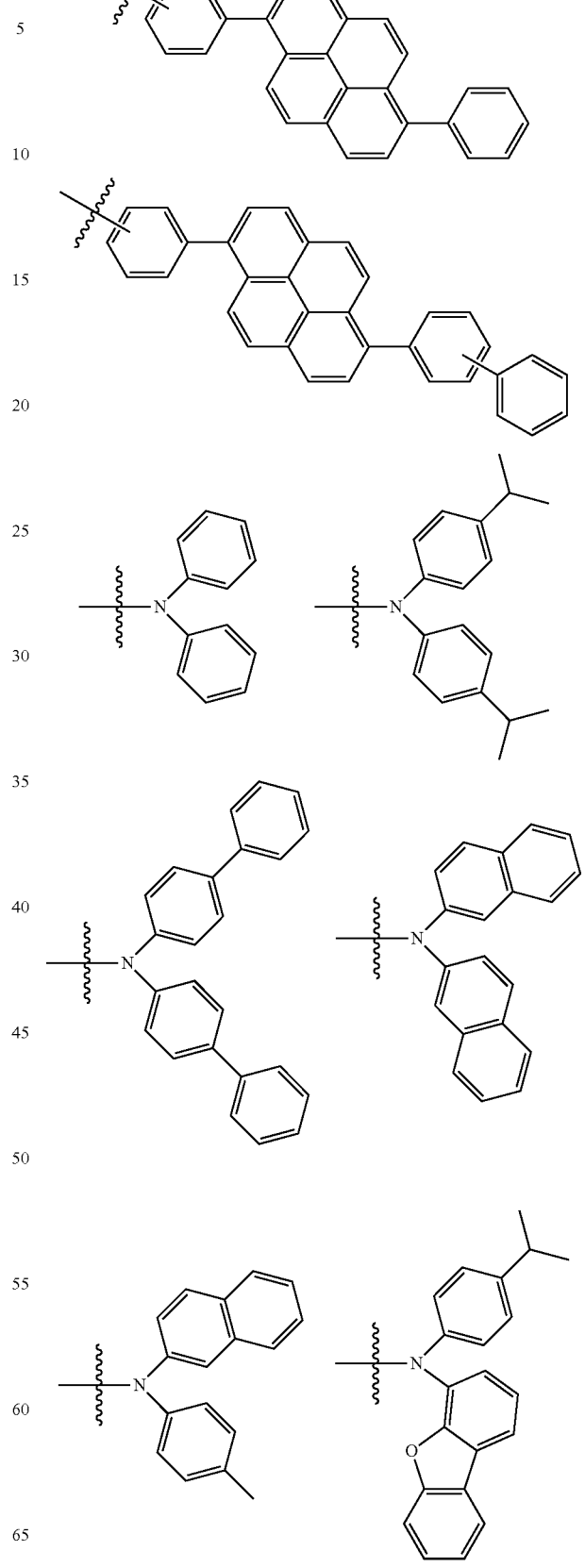

-continued
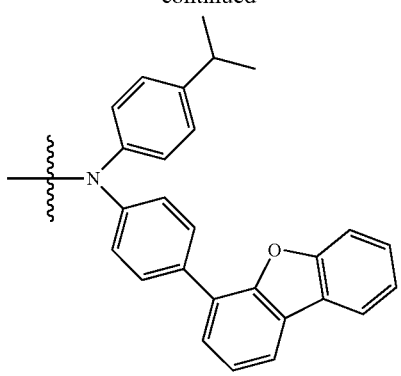
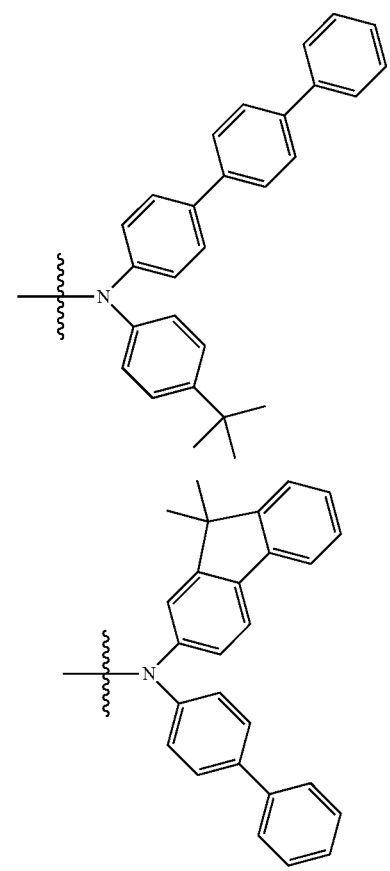
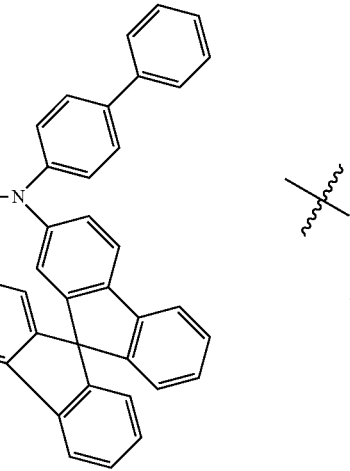
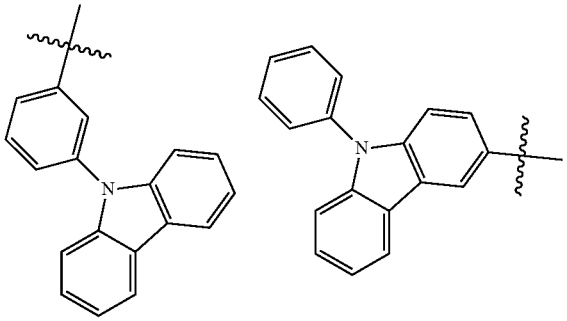
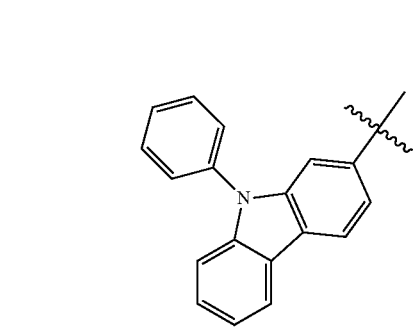
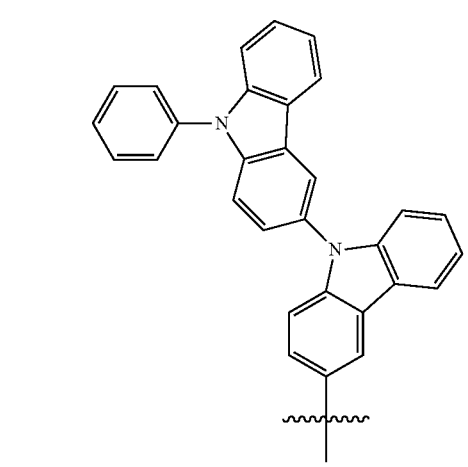
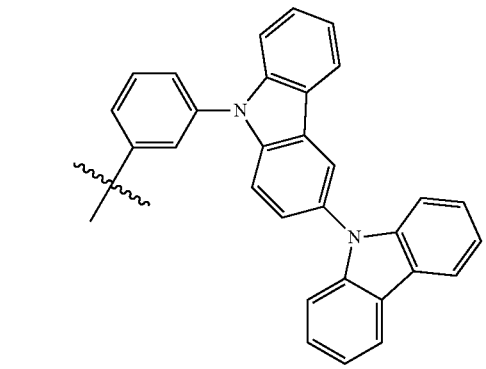

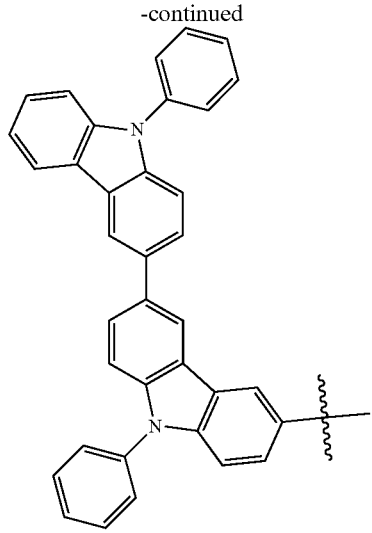
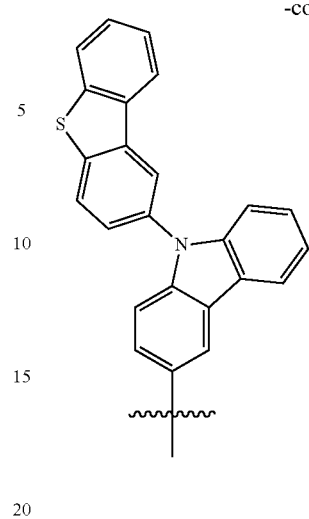
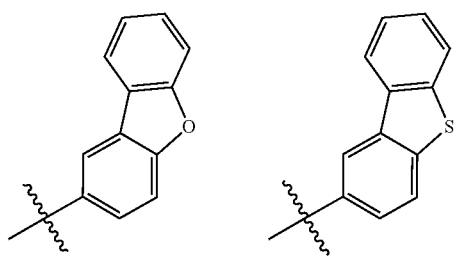
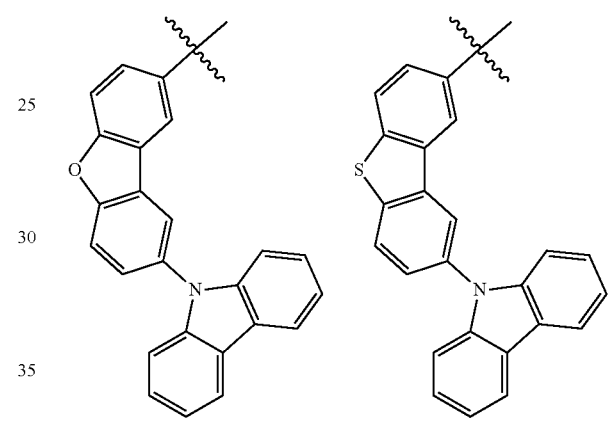
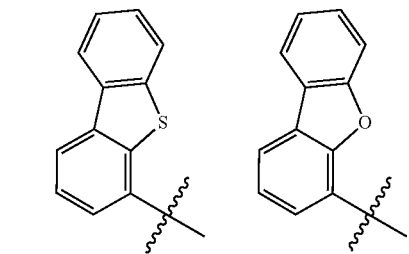
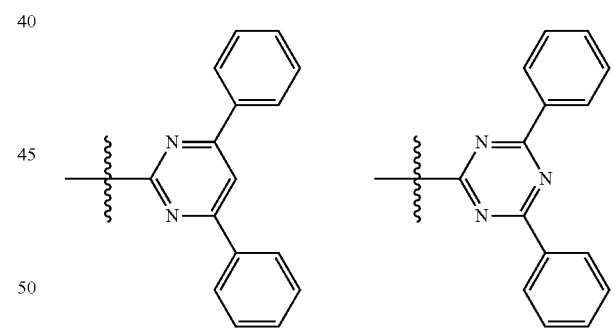
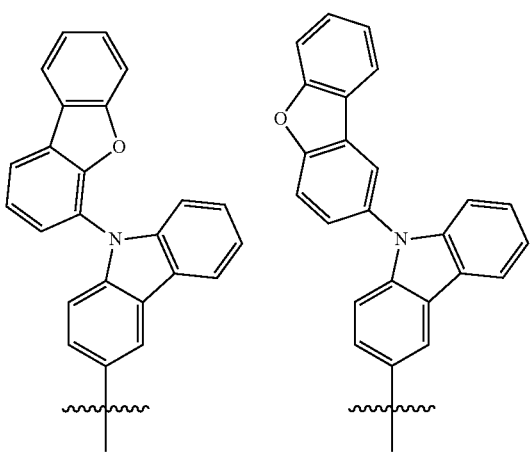
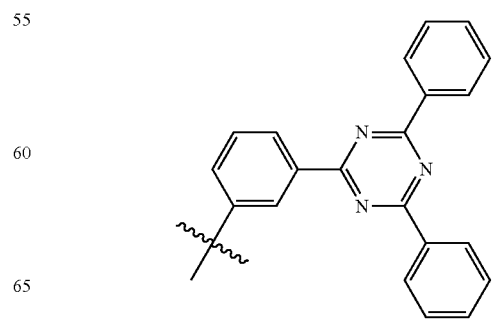

-continued
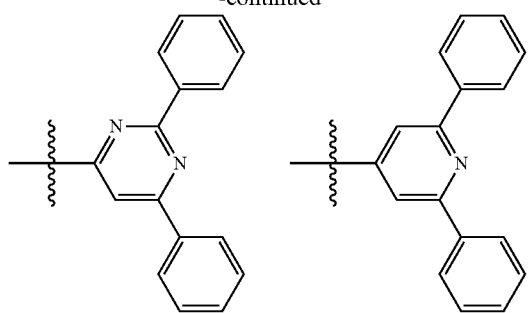
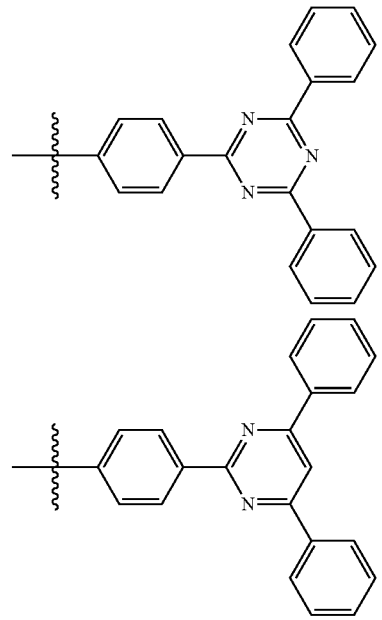
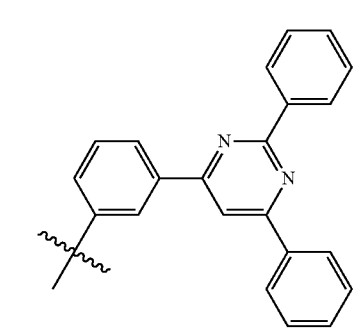
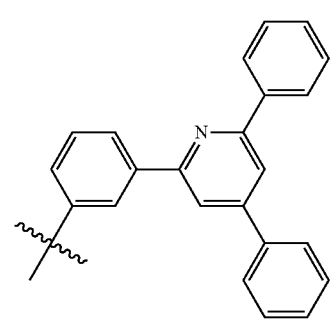
-continued
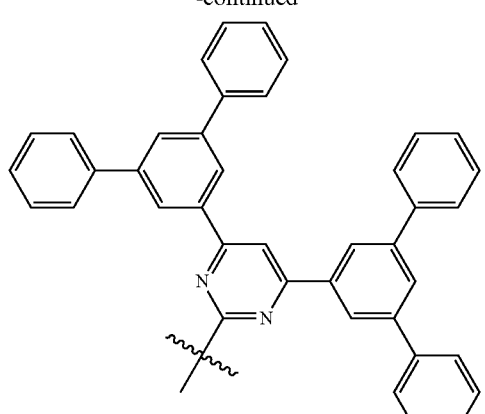
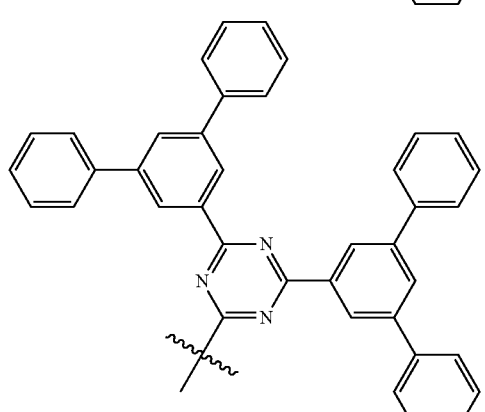
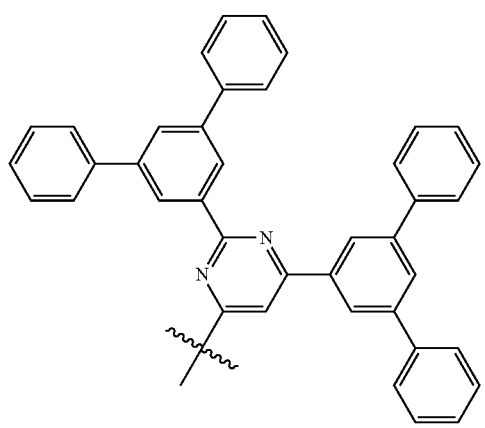
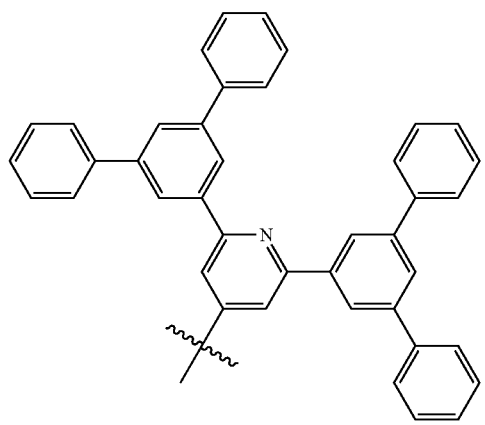

31
-continued
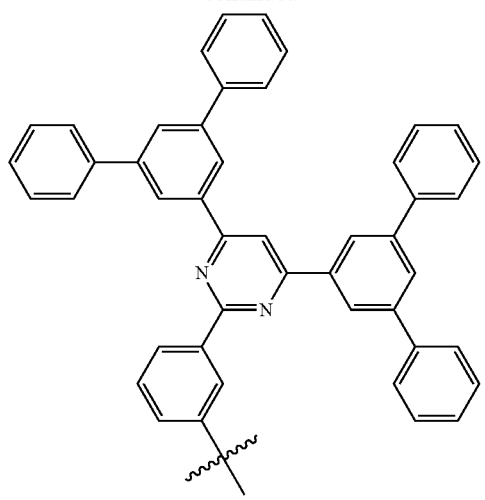
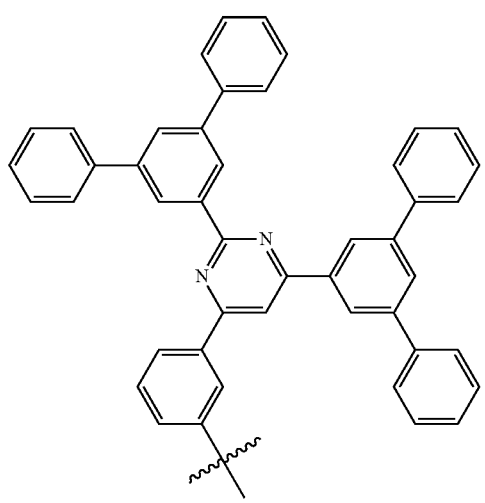
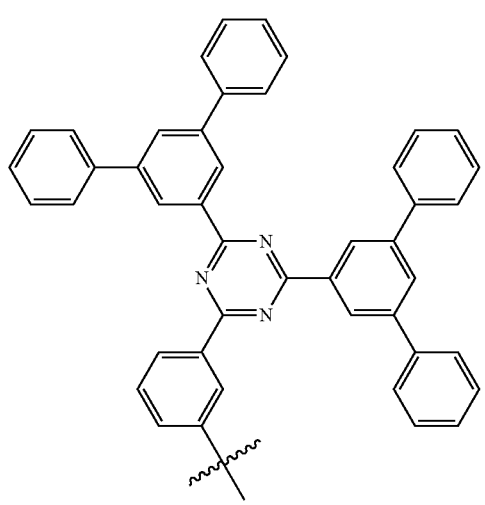
32
-continued
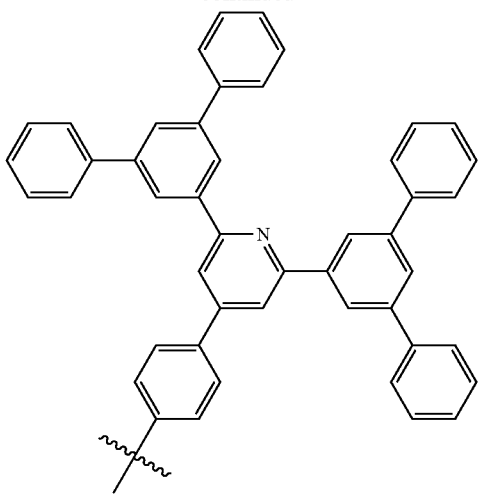
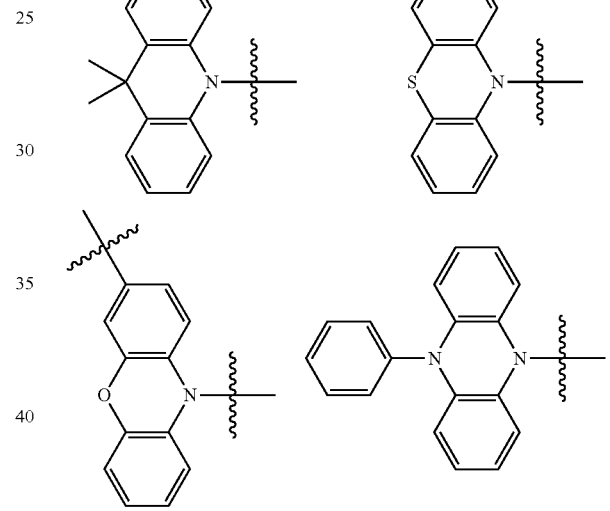
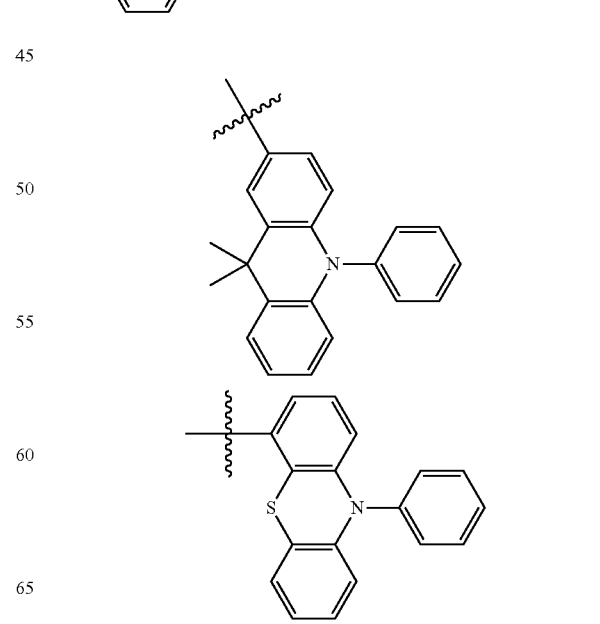

33
-continued
34
-continued
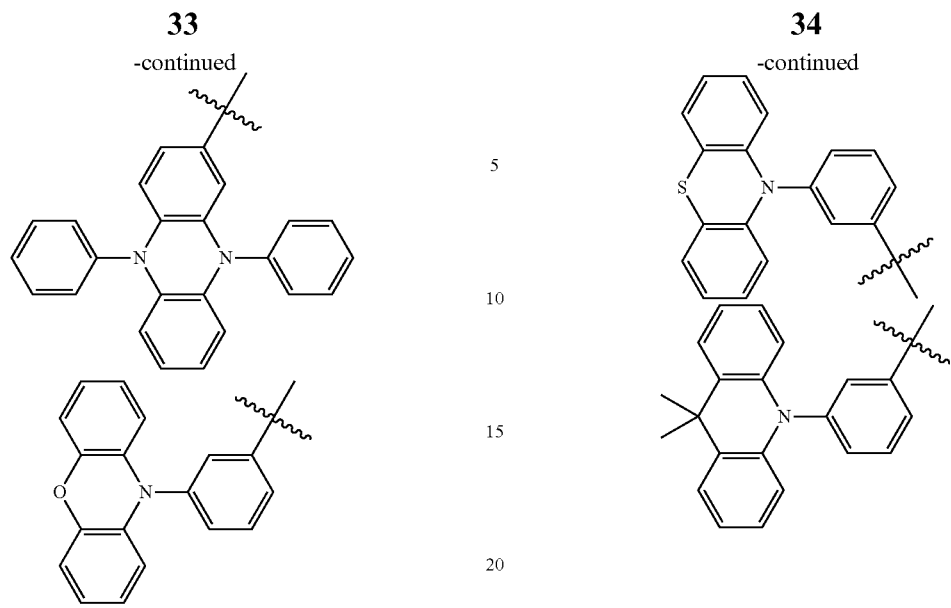
In this embodiment, some material are shown below:
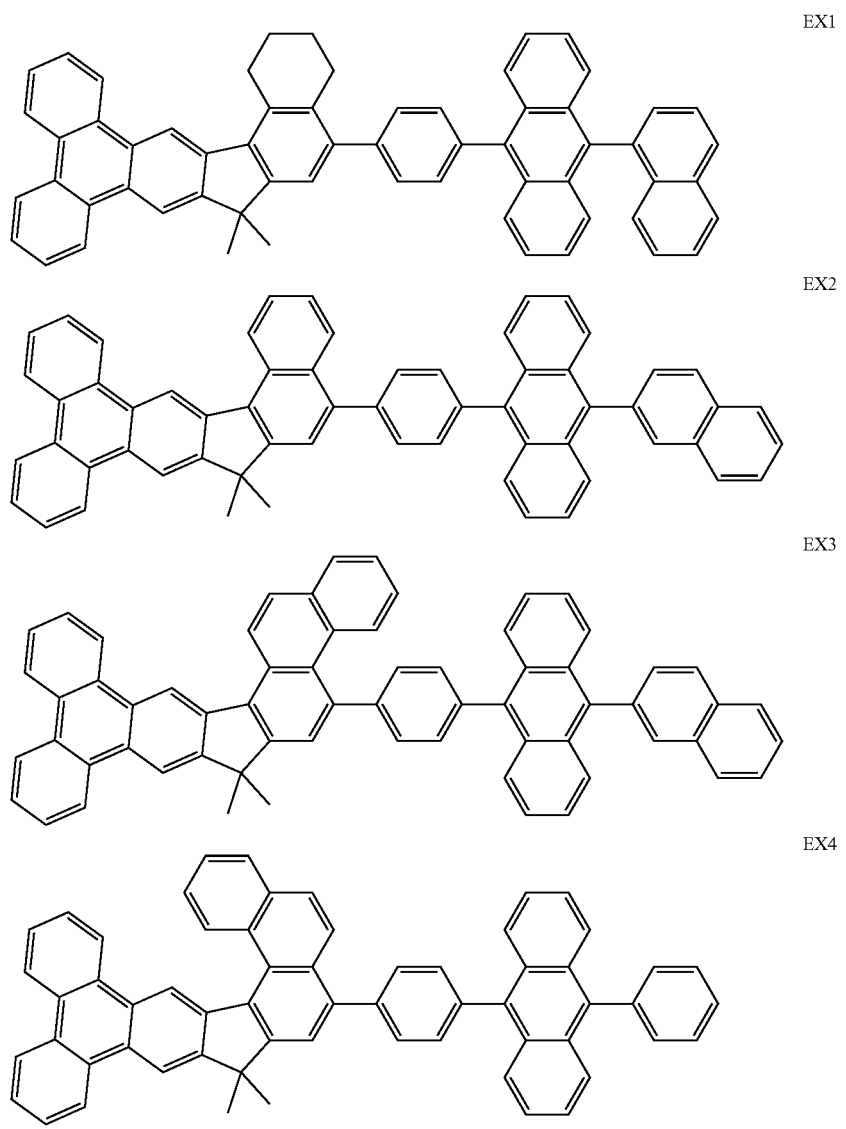

EX5
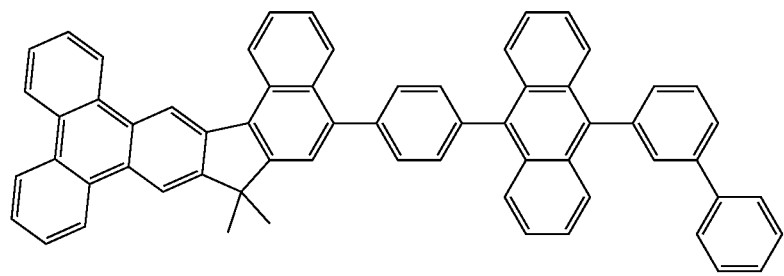
EX6
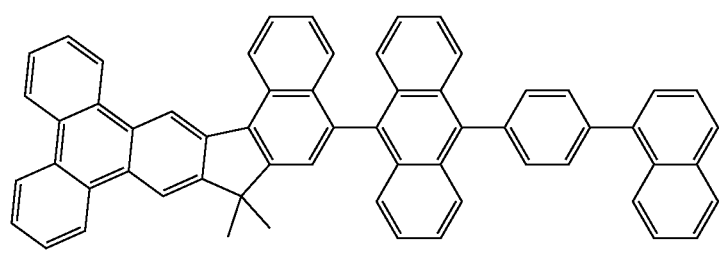
EX7
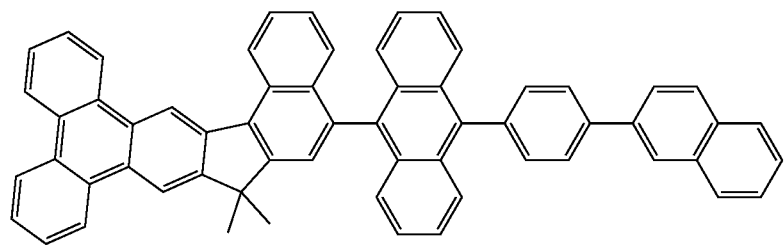
EX8
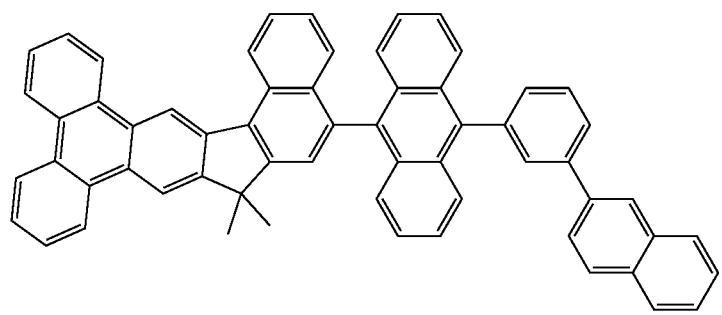
EX9
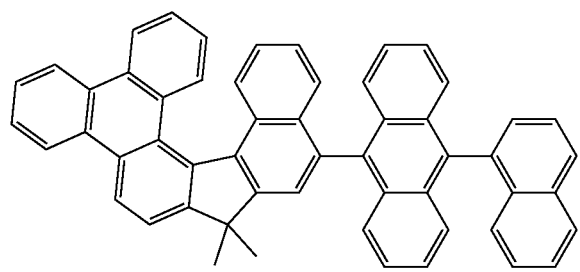

-continued
EX10
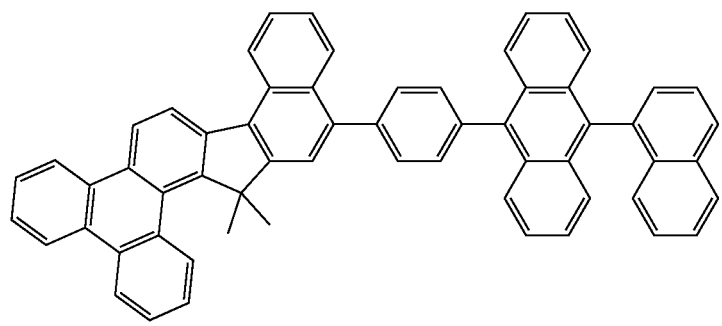
EX11
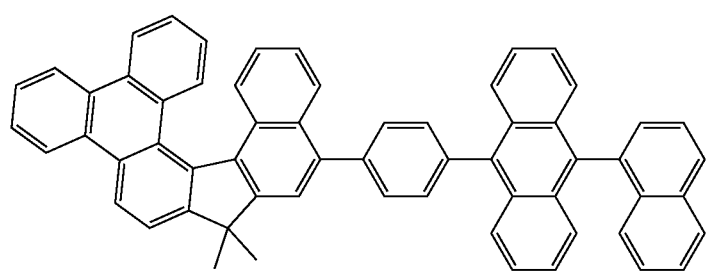
EX12
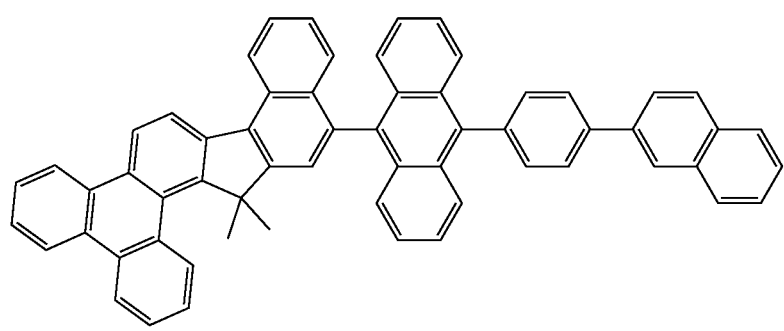
EX13
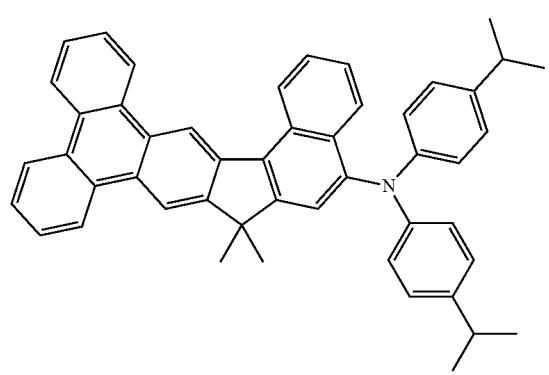

-continued
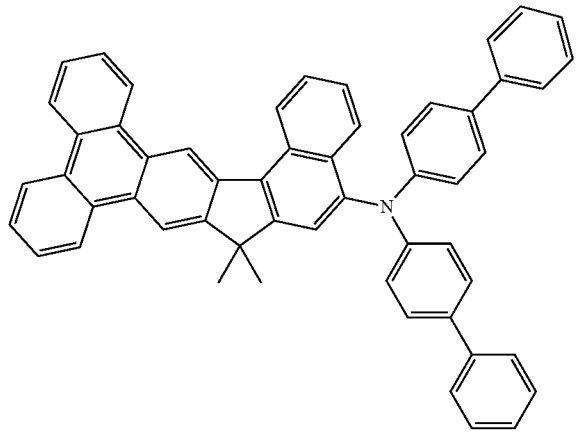
EX14
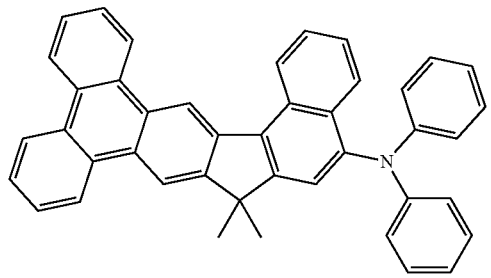
EX15
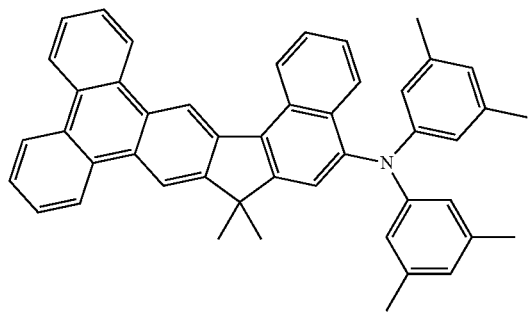
EX16
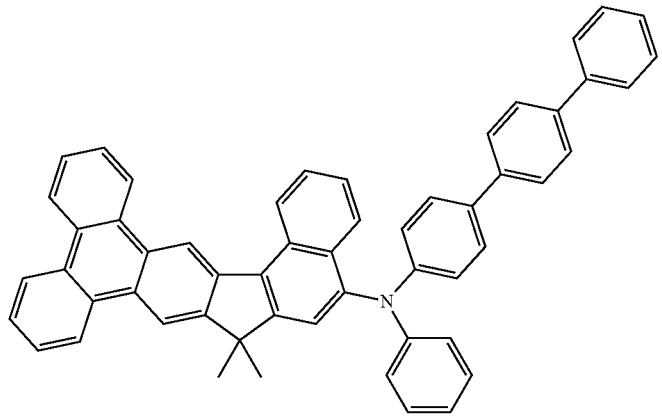
EX17

-continued
EX18
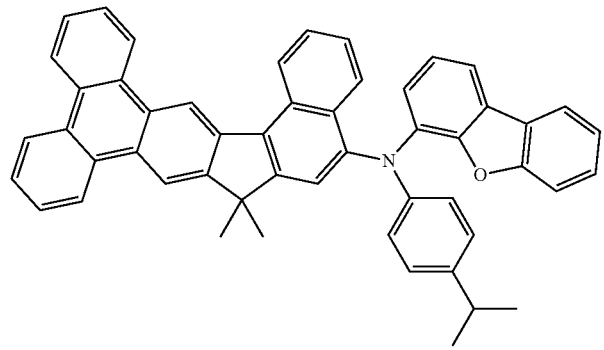
EX19
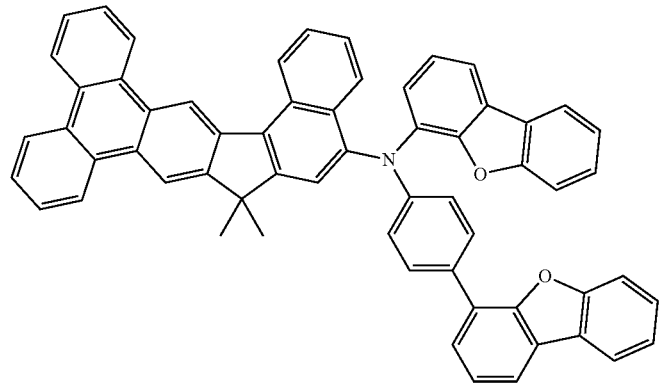
EX20
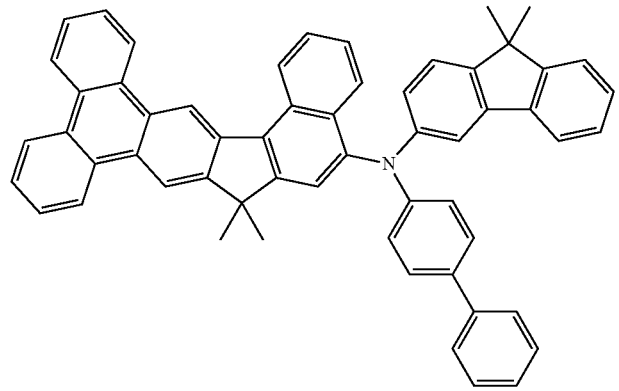
EX21
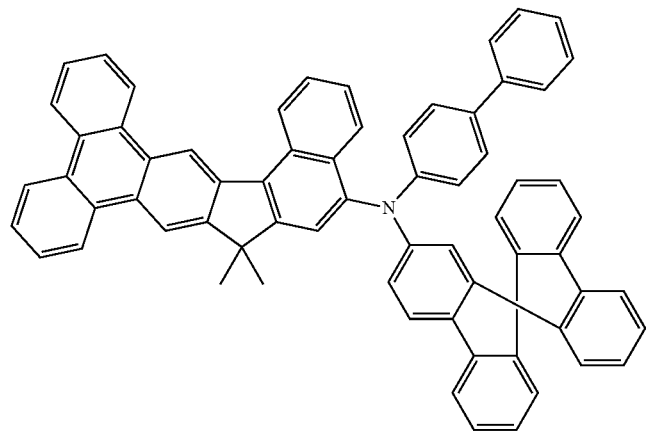

-continued
EX22
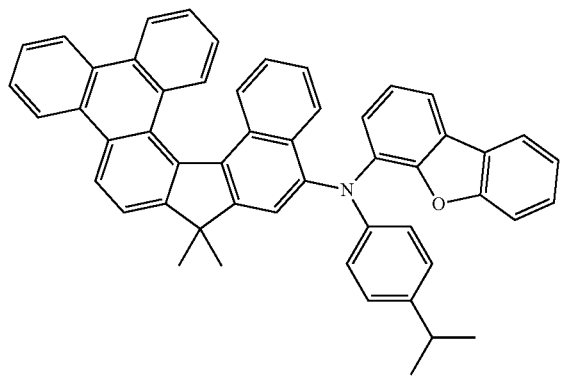
EX23
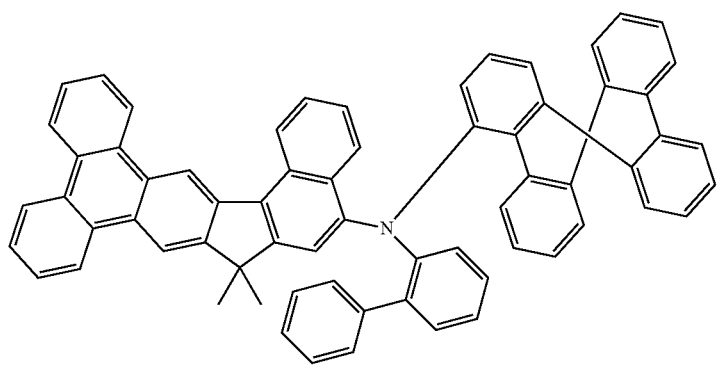
EX24
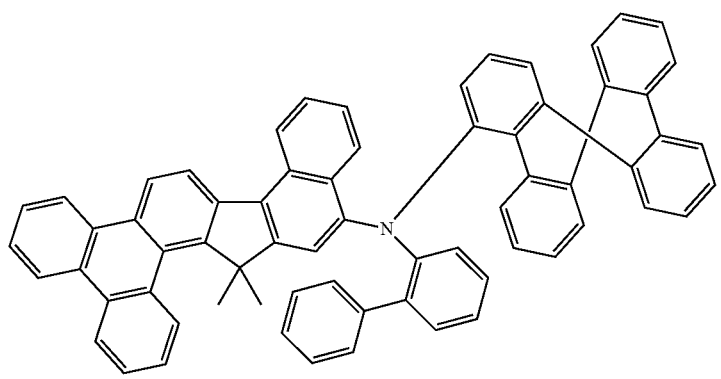
EX25
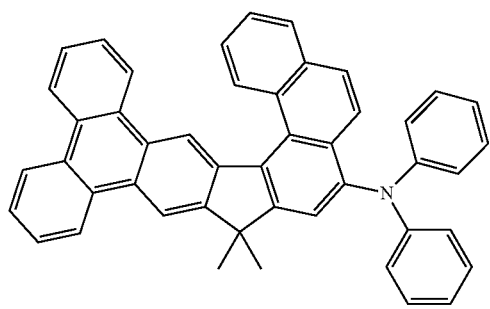

-continued
EX26
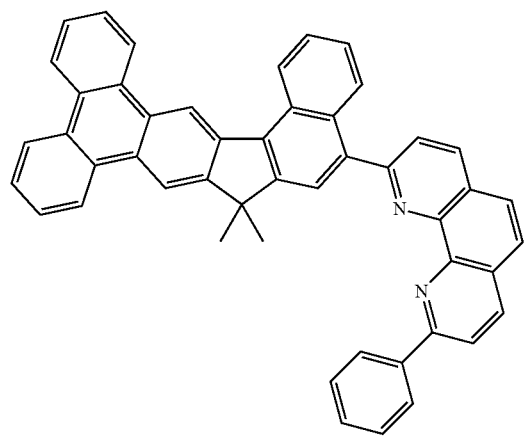
EX27
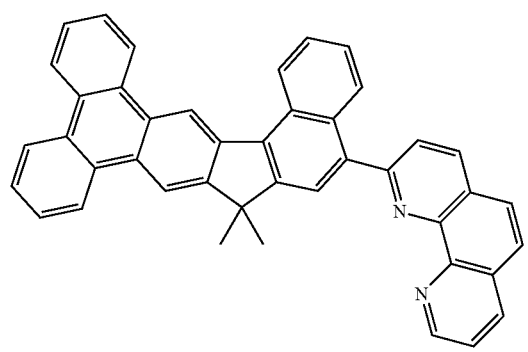
EX28
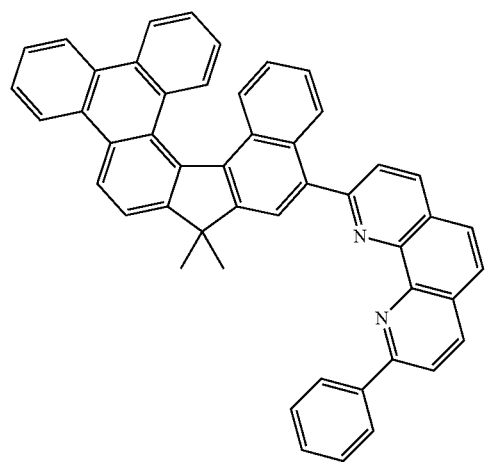
EX29
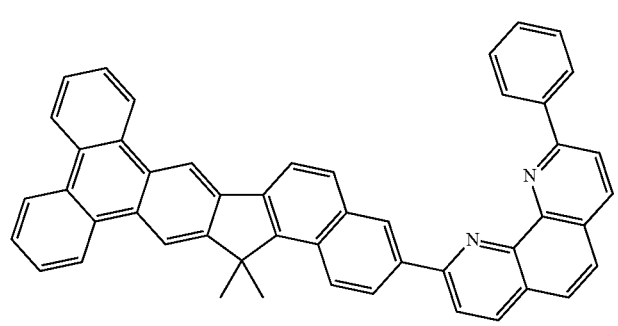

-continued
EX30
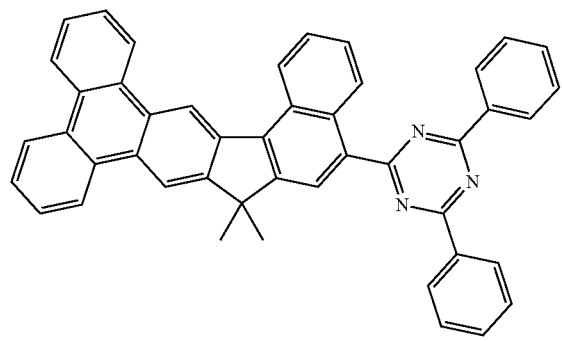
EX31
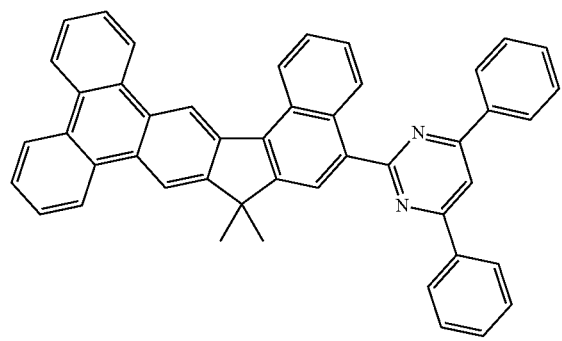
EX32
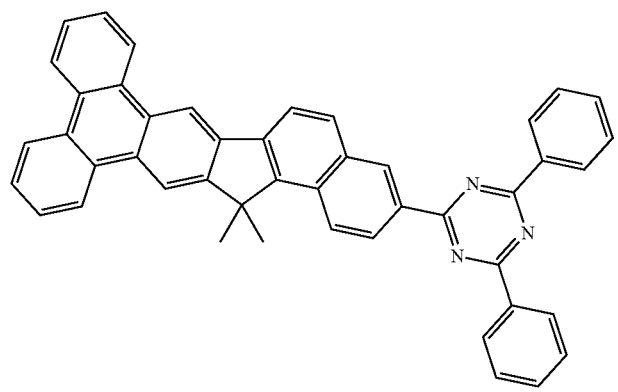
EX33
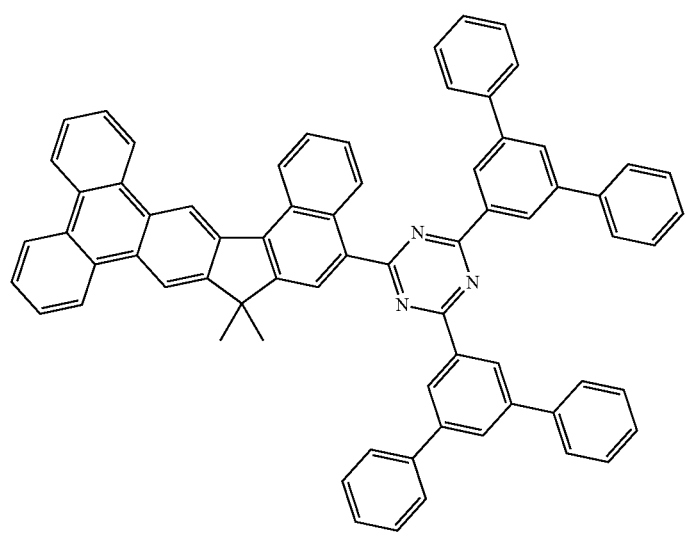

EX34
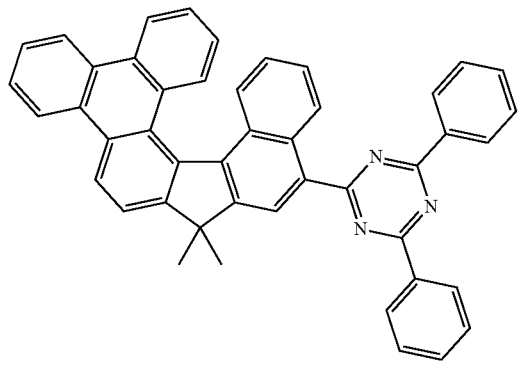
EX35
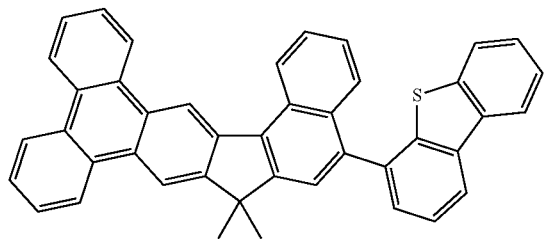
EX36
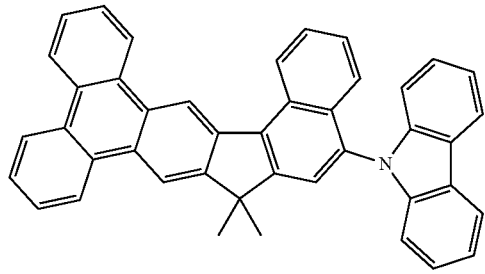
EX37
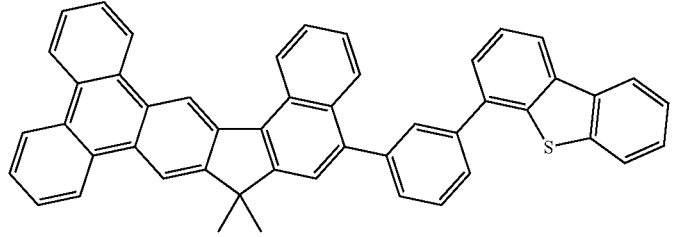
EX38
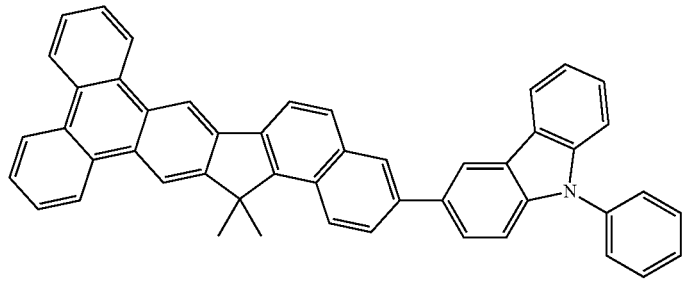

-continued
EX39
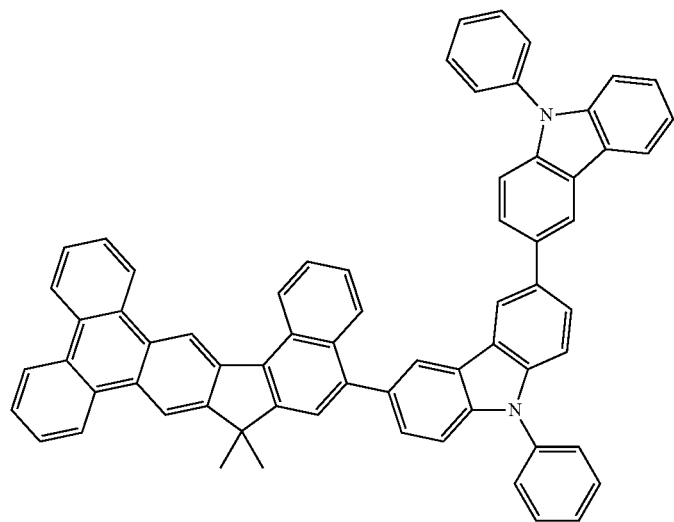
EX40
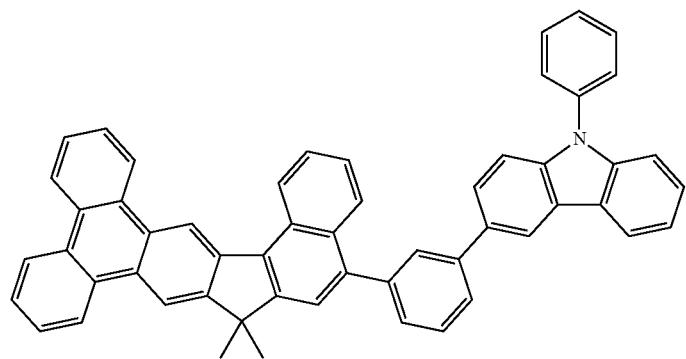
EX41
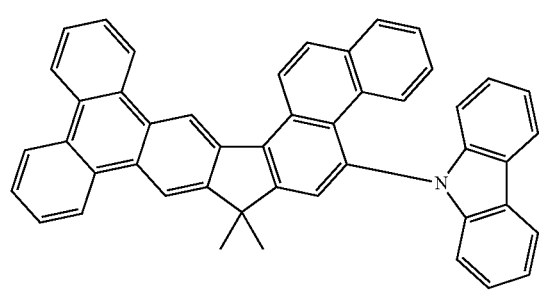
EX42
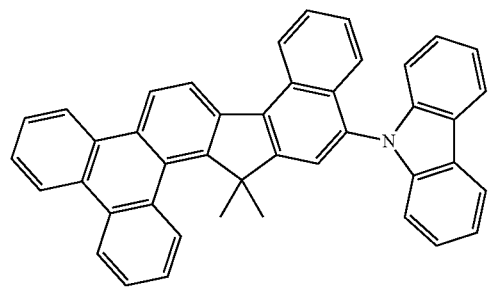

EX43

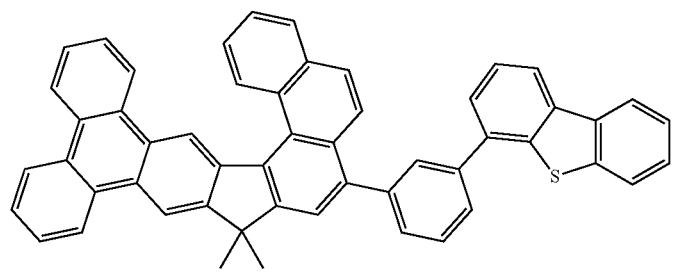

Detailed preparation for the material in the present invention could be clarified by exemplary embodiments, but the present invention is not limited to exemplary embodiments. EXAMPLE 1~5 show the preparation for some EXAMPLES of the material in the present invention. EXAMPLE 6~8 show the fabrication of organic EL device and I-V-B, half-life time of organic EL device testing report.

Synthesis of EX1
Synthesis of 1-bromo-4-methoxynaphthalene

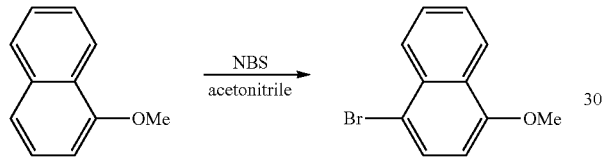

The 50 g(316 of 1-methoxynaphthalene and 600 ml of acetonitrile were added to a reaction vessel. 62 g(348 mmol) of N-bromosuccinimide was added under ice-cooled conditions, and the mixture was stirred for 6 hours and then left for one night. 2000 ml of water was added, the organic layer was extracted with dichloromethane and water, dried with anhydrous magnesium sulfate, the solvent was removed and the residue was purified by column chromatography on silica gel to give product(50.9 g, 215 mmol, 68%).

Synthesis of 4-methoxynaphthalen-1-ylboronic acid

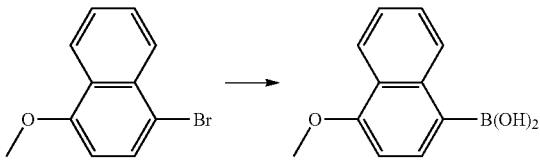

An excess of 1.6 M n-BuLi in hexane(162 ml, 258 mmol) was added to a solution of 1-bromo-4-methoxynaphthalene (50.9 g, 215 mmol) in 800 ml dry tetrahydrofuran at −78° C. under $N_2$. The reaction mixture was then maintained at 0° C. for 1 h before cooling to −78° C. Trimethylborate(35 g, 335 mmol) was added dropwise; the solution was then warmed slowly to room temperature and stirred for 24 h. 2N HCl (250 ml)was added and then the mixture was stirred for a further 1 h. The reaction mixture was extracted with ethyl acetate and water, dried with anhydrous magnesium sulfate, the solvent was evaporated in vacuo, and the residue was crystallized(n-hexane) to give the 4-methoxynaphthalen-1-ylboronic acid (31.8 g, 157 mmol, 61%) as a white solids.

Synthesis of methyl 2-(-4-methoxynaphthalen-1-yl)benzoate

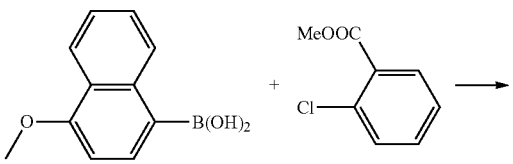

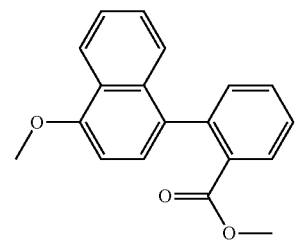

A mixture of 26.8 g(157 mmol) of methyl 2-chlorobenzoate, 31.8 g(157 mmol) of 4-methoxynaphthalen-1-ylboronic acid, 3.5 g(3 mmol) of Pd(PPh$_3$)$_4$, 157 ml of 2M Na$_2$CO$_3$, 200 ml of EtOH and 400 ml of toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product (26.6 g, 91 mmol, 58%) as a white solid.

Synthesis of methyl 2-(2-(4-methoxynaphthalen-1-yl)phenyl)propan-2-ol

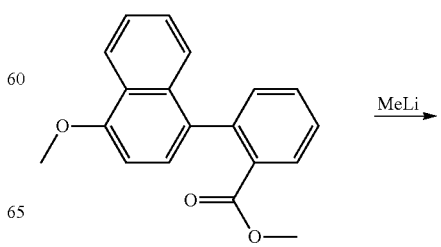

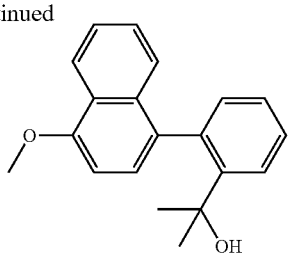

26.601 mmol) of 2-(4-methoxynaphthalen-1-yl)benzoate was placed in a flask, and the flask was made vacuous and tilled with $N_2$. 700 ml of tetrahydrofuran was added, stirring was performed at −78° C. 10 minutes. Subsequently, 284 ml(455 mol) of MeLi(1.6M in hexane) was added thereto, stirred at −78° C. for 10 minutes, and stirred at room temperature for 6 hours. After termination of the reaction, the reaction product was extracted with distilled water and ethyl acetate. The resultant organic layer was dried with IVIgSO4, evaporated using a rotary evaporator to remove the solvent, and subjected to column chromatography using hexane and ethyl acetate as a developing solvent, thus obtaining 20.7 g(78%) of 2-(2-(4-methoxynaphthalen-1-yl) phenyl) propan-2-ol.

Synthesis of 5-methoxy-7,7-dimethyl-7H-benzo(c)fluorene

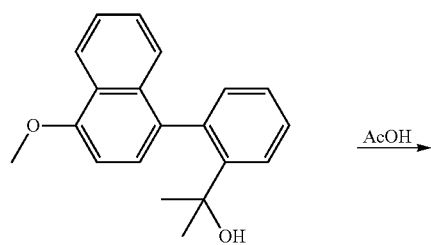

20.7 g(70.8 mmol) of 2-(2-(4-methoxynaphthalen-1-yl) phenyl) propan-2-ol was placed in a flask, and the flask was made vacuous and filled with $N_2$. 200 ml of AcOH was added, stirring was performed at 0° C. 10 minutes. The reaction mixture was added with 400 ml of $H_3PO_4$ and stirred at room temperature for 3 hour. After termination of the reaction, the reaction product was neutralized with NaOH, and extracted with distilled water and ethyl acetate. The resultant organic layer was dried with $MgSO_4$, evaporated using a rotary evaporator to remove the solvent, and subjected to column chromatography using hexane and ethyl acetate as a developing solvent, thus obtaining 16.7 g(86%) of 5-methoxy-7,7-dimethyl-7H-benzo[c]fluorene.

Synthesis of 9-bromo-5-methoxy-7,7-dimethyl-7H-benzo(c)fluorene

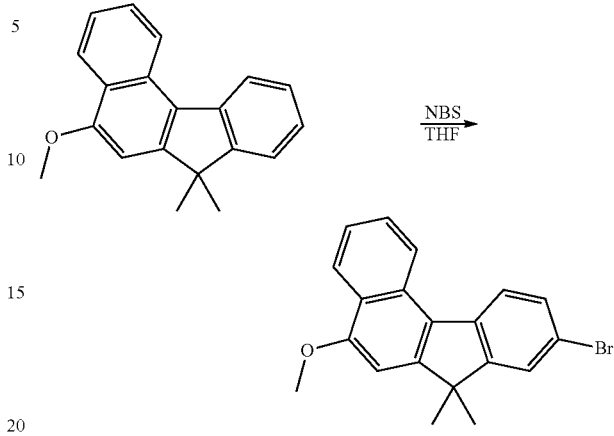

16.7 g(60.9 mmol) of 5-methoxy-7,7-dimethyl-7H-benzo [c] fluorene was placed in a flask, and the flask was made vacuous and filled with $N_2$. 340 ml of tetrahydrofuran was added thereto, stirring was performed at 0° C. for 10 minutes. Subsequently, the reaction mixture was added with 11.9 g (67 mmol) of NBS and stirred at room temperature for 30 minutes. After termination of the reaction, the reaction product was extracted with distilled water and ethyl acetate. The resultant organic layer was dried with $MgSO_4$, evaporated using a rotary evaporator to remove the solvent, and subjected to column chromatography using hexane and ethyl acetate as a developing solvent, thus obtaining 18 g(84%) of 9-bromo-5-methoxy-7,7-dimethyl-7H-benzo[c]fluorene Synthesis of 9-(biphenyl-2-yl)-5-methoxy-7,7-dimethyl-7H-benzo(c)fluorene

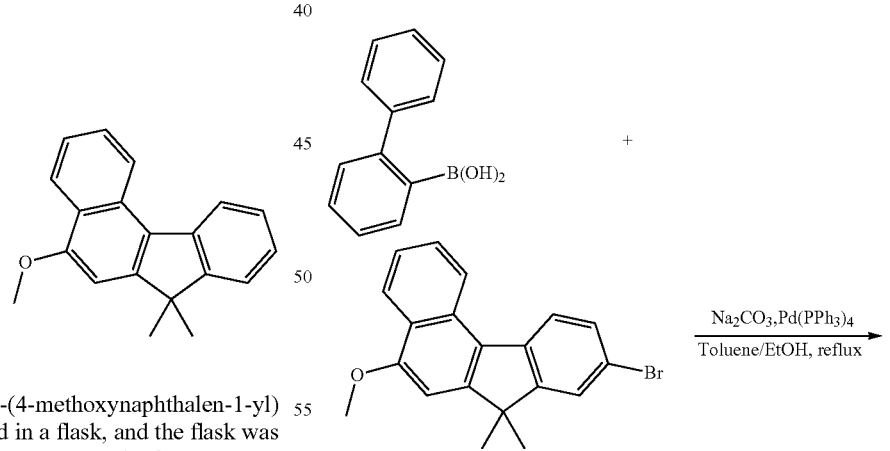

A mixture of 35.3 g(100 mmol) of 9-bromo-5-methoxy-7,7-dimethyl-7H-benzo[c]fluorene, 21.8 g(110 mmol) of biphenyl-2-ylboronic acid, 2.31 g(2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (31.1 g, 73.0 mmol, 73%) as a white solid.

Synthesis of intermediate I

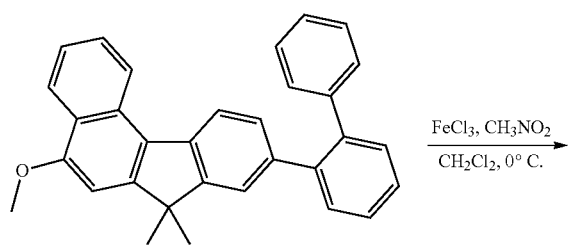

intermediate I

In a 3000 ml three-necked flask that had been degassed and filled with nitrogen, 25.6 g(60 mmol) of 9-(biphenyl-2-yl)-5-methoxy-7,7-dimethyl-7H-benzo[c]fluorene was dissolved in anhydrous dichloromethane (1500 ml), 97.5 g(600 mmol) Iron(III) chloride was then added, and the mixture was stirred one hour. Methanol 500 ml were added to the mixture and the organic layer was separated and the solvent removed in vacuo. The residue was purified by column chromatography on silica gel(hexane-dichloromethane) afforded a white solid(15.5 g, 36.6 mmol, 61%).

Synthesis of intermediate II

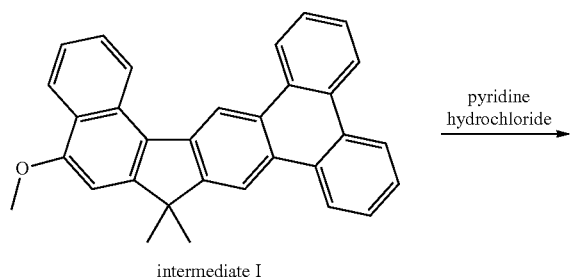

intermediate I

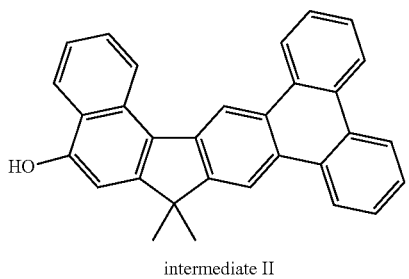

intermediate II

A mixture of 4.9 g(11.6 mmol) of intermediate I, 13.4 g(1168 mmol) of pyridine hydrochloride, was degassed and placed under nitrogen, and then heated at 220° C. for 6 h, the mixture was allowed to cool to room temperature and water was added. The resulting solid was filtered off, washed with water, and dried under high vacuum to give product (4.4 g, 10.8 mmol, 93%).

Synthesis of intermediate III

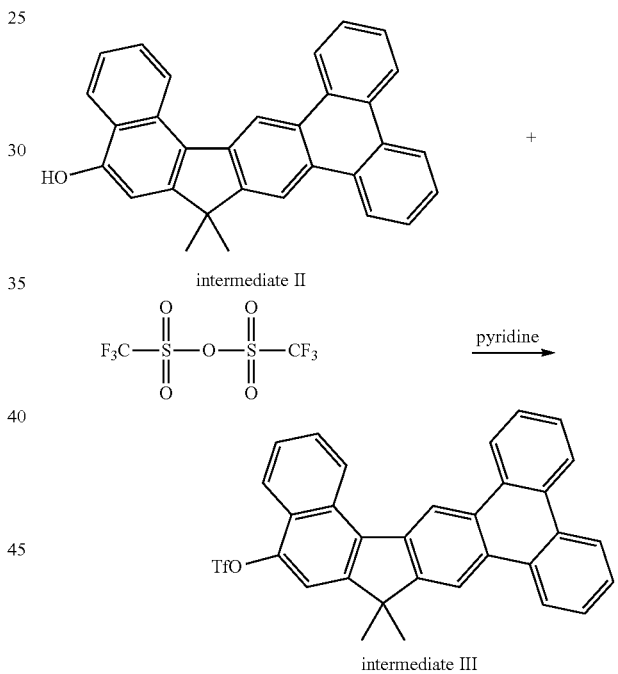

intermediate III

In a 1000 ml three-necked flask that had been degassed and filled with nitrogen, 4.1 g(10.0 mmol) of intermediate II was dissolved in anhydrous dichloromethane(660 ml), 20 ml pyridine was then added, and the mixture was cooled in an ice salt bath. 6.8 ml(40 mmol) trifluoromethanesulfonic anhydride in 40 ml dichloromethane was added dropwise to the solution under nitrogen, the reaction was allowed to proceed for 6 hours and quenched by adding methanol and water. The resulting solid was filtered off, washed with water, methanol and dichloromethane, the residue product was recrystallized from toluene. 4.0 g(7.4 mmol, 74%) product was obtained. $^1$H NMR (CDCl3, 400 MHz): chemical shift(ppm) 9.55 (s, 1H), 9.07 (d, J=8.0 Hz, 1H), 8.72 (d, J=8.0 Hz, 1H), 8.77~8.74 (m, 2H), 8.71~8.66 (m, 2H), 8.22 (d, J=8.0 Hz, 1H), 7.91~7.63 (m, 7H), 1.71 (m, 6H)

Synthesis of intermediate IV

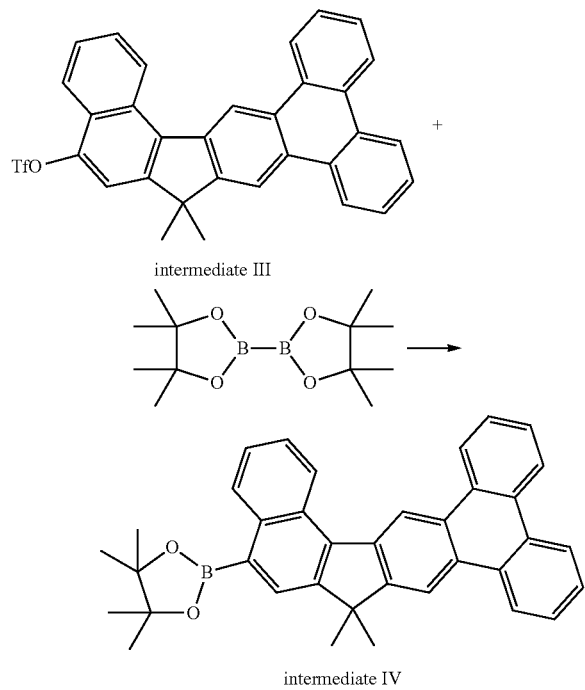

intermediate III intermediate IV

A mixture of 3.7 g(6.8 mmol) of intermediate III, 7 g(27.2 mmol) of bis(pinacolato)diboron, 0.36 g(0.31 mmol) of tetrakis (triphenylphosphine) palladium, 4 g(40.56 mmol) of potassium acetate, and 200 ml of 1,4-dioxane was degassed and placed under nitrogen, and then heated at 120° C. for 24 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 2.4 g of light yellow product (yield 67%).

Synthesis of EX1

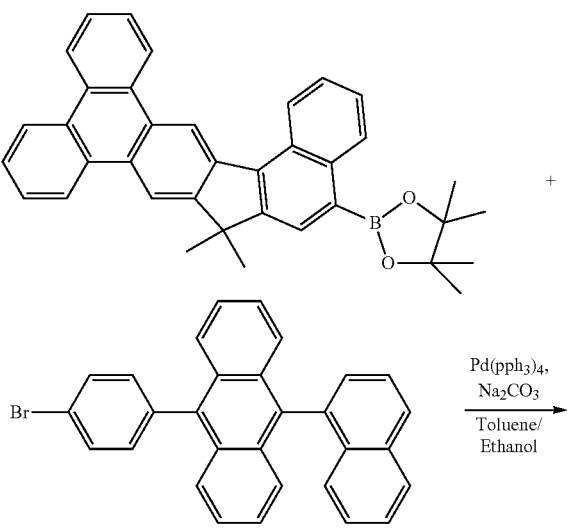

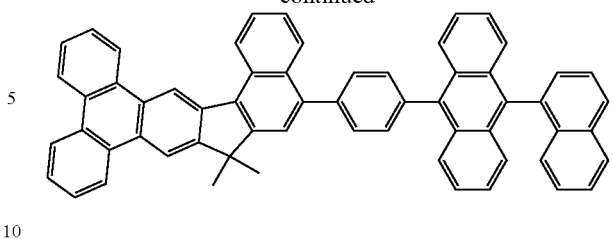

A mixture of 2.0 g(3.8 mmol) of intermediate IV, 1.9 g(4.2 mmol) of 9-(4-bromophenyl)-10-(naphthalen-1-yl)anthracene, 0.11 g(0.1 mmol) of tetrakis(triphenylphosphine)palladium, 5 ml of 2M $Na_2CO_3$, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was purified by column chromatography on silica(Hx~EA) to give product 1.7 g(57%). MS(m/z, FAB+):772.2

Synthesis of EX13
Synthesis bis(4-isopropylphenyl)amine

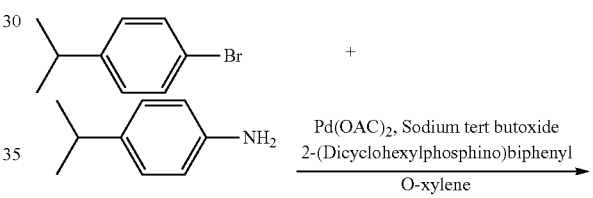

A mixture of 10 g(50 mmol) 1-bromo-4-isopropylbenzene, 7.4 g(55 mmol) of 4-isopropylaniline, 0.25 g(1 mmol) of palladium(II)acetate, 0.75 g(2.0 mmol) of 2-(dicyclohexylphosphino)biphenyl, 9.6 g(100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 4.7 g(yield 37%) of yellow product which was recrystallized from hexane.

Synthesis of EX2

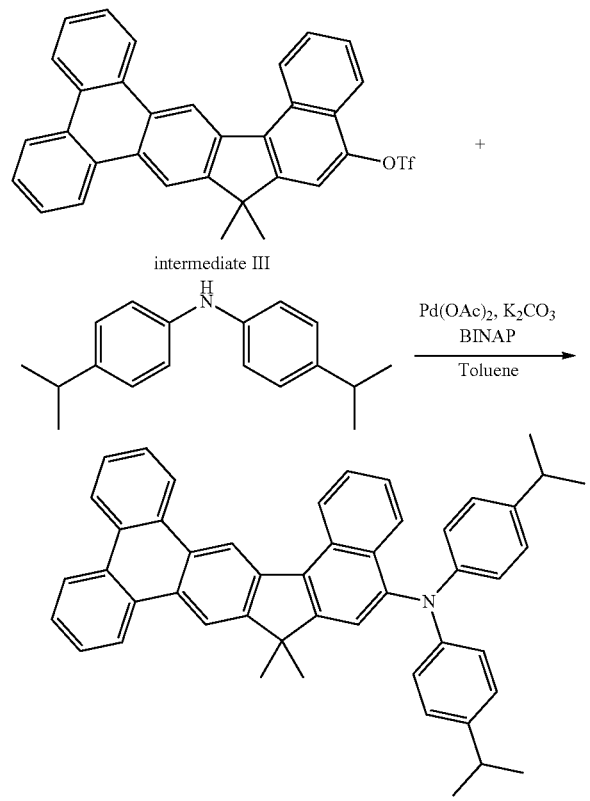

A mixture of 3.2 g(6 mmol) of intermediate III, 1.5 g(6 mmol) of, bis(4-isopropylphenyl)amine 0.1 g(0.4 mmol) of palladium(II)acetate, 0.48 g of BINAP, 4 g of potassium carbonate and 50 ml toluene was degassed and placed under nitrogen, and then heated at 110° C. overnight. After finishing the reaction, the mixture was allowed to cool to room temperature. Than 200 ml of MeOH was added, while stirring and the precipitated product was filtered off with suction. To give 2.3 g(yield 61%) of yellow product which was recrystallized from ethyl acetate. MS(m/z,FAB+):645.6

Synthesis of EX23
Synthesis N-(biphenyl-2-yl)-9-9'-spirobi[fluoren]-4-amine

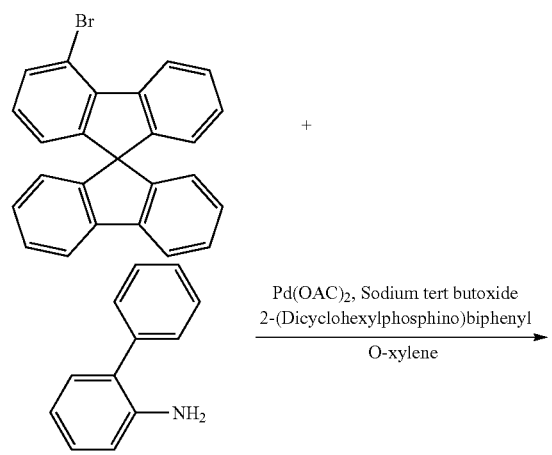

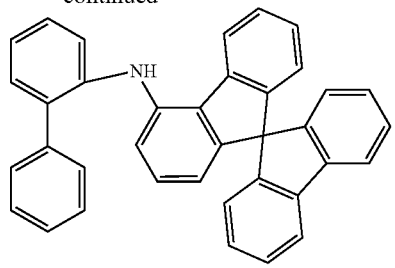

A mixture of 19.8 g(50 mmol) 4-bromo-9,9'-spirobi[fluorene], 9.3 g(55 mmol) of biphenyl-2-amine, 0.25 g(1 mmol) of palladium(II)acetate, 0.75 g(2.0 mmol) of 2-(dicyclohexylphosphino)biphenyl, 9.6 g(100 mmol)of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 12.3 g(yield 51%) of yellow product which was recrystallized from hexane.

Synthesis of EX3

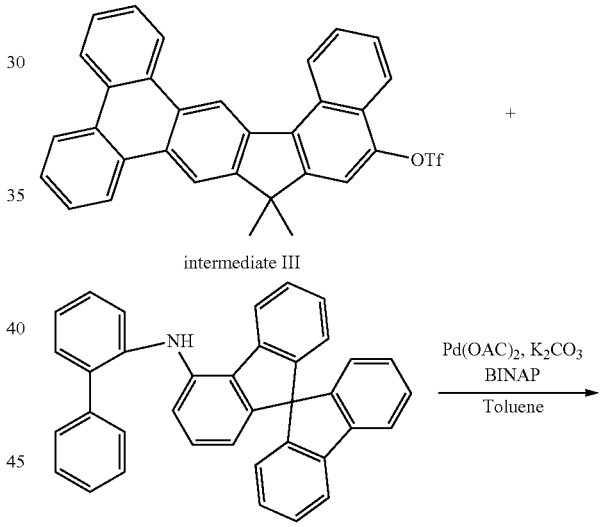

A mixture of 3.2 g(6 mmol) of intermediate III, 2.9 g(6 mmol) of, N-(biphenyl-2-yl)-9,9'-spirobi[fluoren]-4-amine 0.1 g(0.4 mmol) of palladium(II) acetate, 0.48 g of BINAP, 4 g of potassium carbonate and 50 ml toluene was degassed and placed under nitrogen, and then heated at 110° C. overnight. After finishing the reaction, the mixture was allowed to cool to room temperature. Than 200 ml of MeOH was added, while stirring and the precipitated product was filtered off with suction. To give 1.9 g(yield 37%) of yellow product which was recrystallized from ethyl acetate. MS(m/z,FAB+):875.6

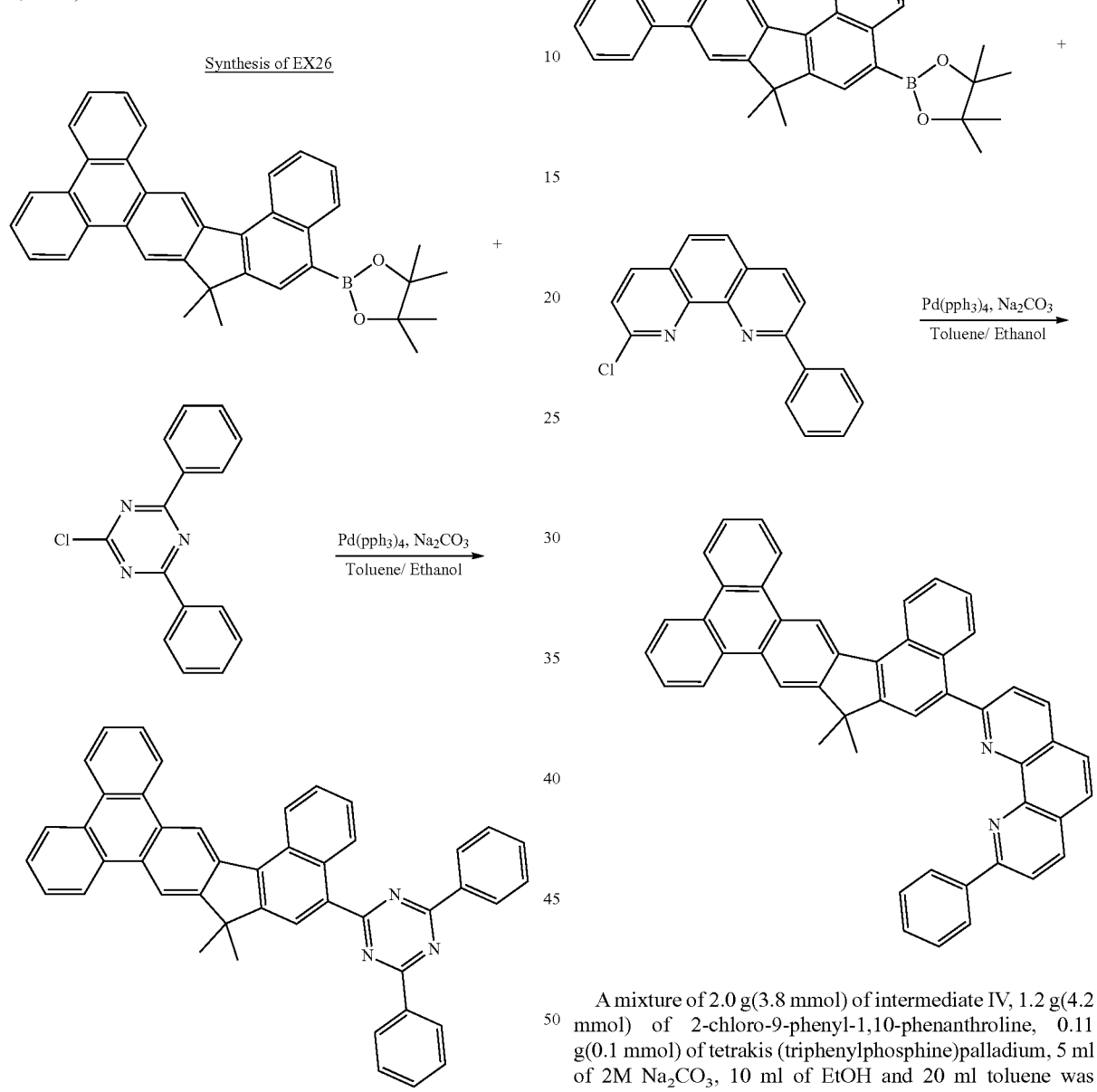

A mixture of 2.0 g(3.8 mmol) of intermediate IV, 1.1 g(4.2 mmol) of 2-chloro-4,6-diphenyl-1,3,5-triazine, 0.11 g(0.1 mmol) of tetrakis(triphenylphosphine)palladium, 5 ml of 2M Na₂CO₃, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was purified by column chromatography on silica(Hx-EA) to give product 1.7 g(71%). MS(m/z, FAB+):625.2

A mixture of 2.0 g(3.8 mmol) of intermediate IV, 1.2 g(4.2 mmol) of 2-chloro-9-phenyl-1,10-phenanthroline, 0.11 g(0.1 mmol) of tetrakis (triphenylphosphine)palladium, 5 ml of 2M Na₂CO₃, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was recrystallized from dichloromethane to give product 2 g(83%). MS(m/z, FAB+):648.1

General Method of Producing Organic EL Device

ITO-coated glasses with 9~12 ohm/square in resistance and 120~160 nm in thickness are provided(hereinafter ITO substrate) and cleaned in a number of cleaning steps in an ultrasonic bath(e.g. detergent, deionized water). Before vapor deposition of the organic layers, cleaned ITO substrates are further treated by UV and ozone. All pre-treatment processes for ITO substrate are under clean room(class 100).

These organic layers are applied onto the ITO substrate in order by vapor deposition in a high-vacuum unit($10^{-7}$ Torr), such as: resistively heated quartz boats. The thickness of the respective layer and the vapor deposition rate(0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine(NPB) is most widely used as the hole transporting layer. N-(biphenyl-4-yl)-9,9-dimethyl-N-(4'-phenylbiphenyl-4-yl)-9H-fluoren-2-amine(EB2) is used as electron blocking layer, 10,10-Dimethyl-12-(4-(pyren-1-yl)phenyl)-10H-indeno[1,2-b]triphenylene (PT-312) is used as blue emitting host and N1,N1,N6,N6-tetram-tolylpyrene-1,6-diamine(D1) is used as blue guest. 2-(10,10-dimethyl-10H-indeno[2,1-b]triphenylen-13-yl)-9-phenyl-1,10-phenanthroline is used as electron transporting material (ET1) to co-deposit with 5% Li,2-(10,10-dimethyl-10H-indeno[2,1-b]triphenylen-12-yl)-4,6-diphenyl-1,3,5-triazine is used as electron transporting material(ET2) to co-deposit with 8-hydroxyquinolato-lithium(LiQ) in organic EL device. Bis(2-methyl-8-quinolinolate)-4-(phenylphenolato)aluminium(BAlq) is used as hole blocking material(HBM) and phosphorescent host for phosphorescent system. Bis(2-phenylpyridinato) (2,4-diphenylpyridinato)iridium(III) (D2) are used as phosphorescent dopant. The prior art of OLED materials for producing standard organic EL device control, comparable materials and EXAMPLES in this invention shown its chemical structure as following:

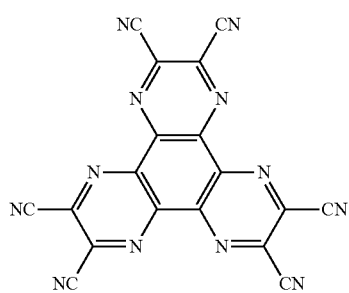

HAT-CN

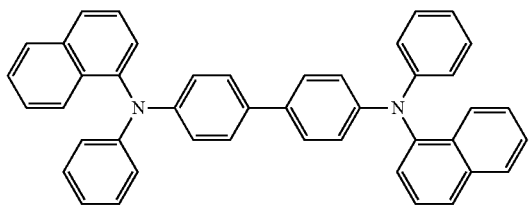

NPB

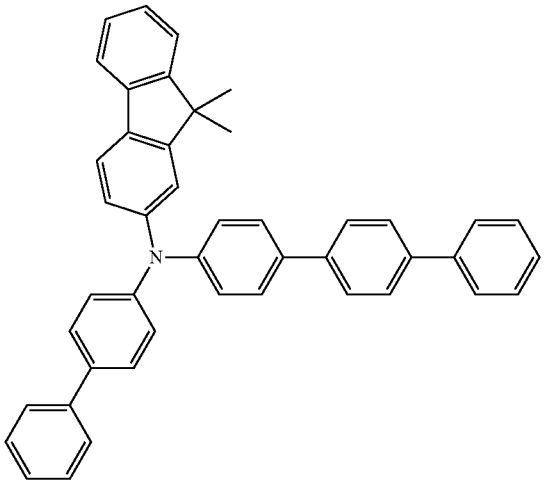

EB2

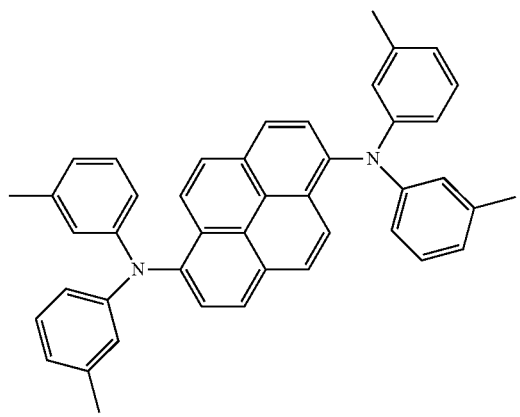

D1

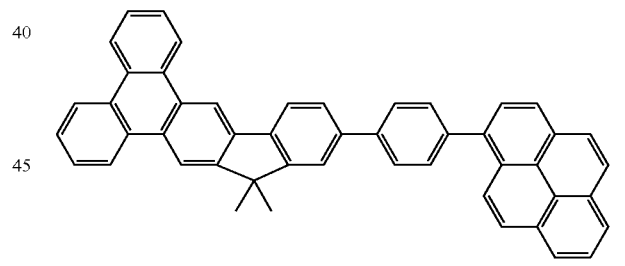

PT-312

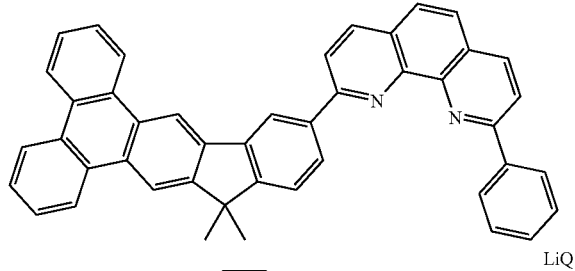

ET1

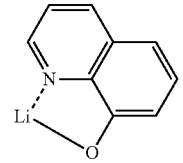

LiQ

ET2
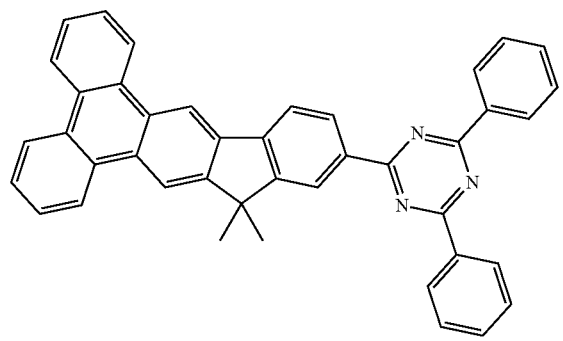
BAlq
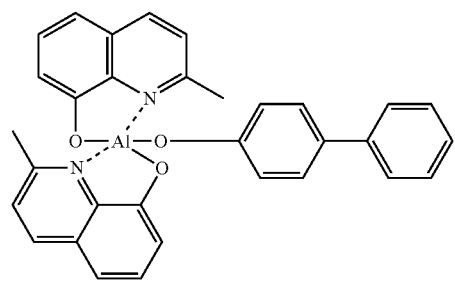
D2
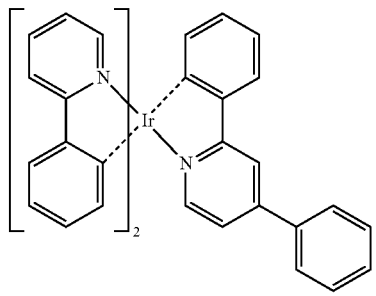
EX1
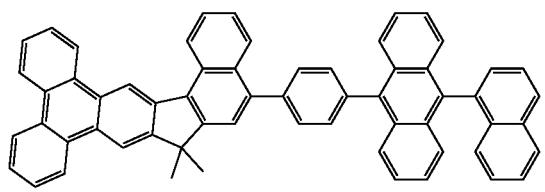
EX13
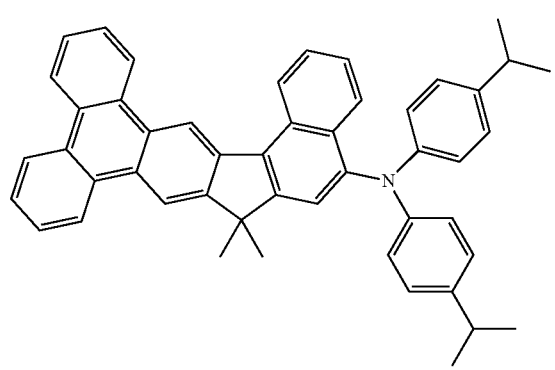
EX23
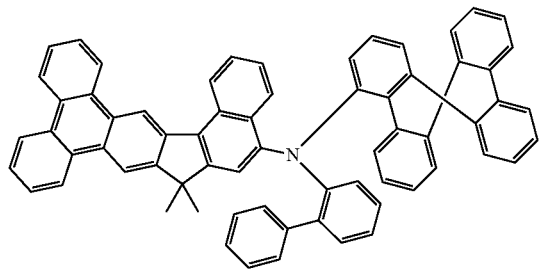
EX26
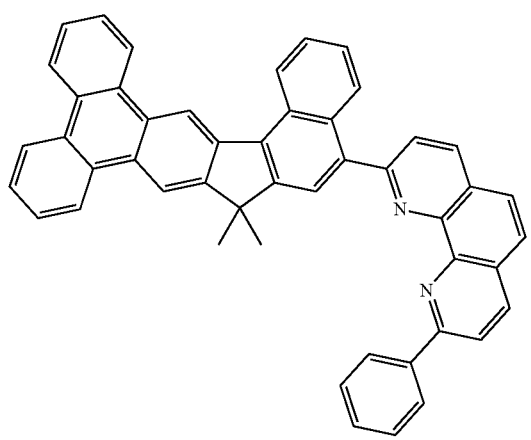
EX30
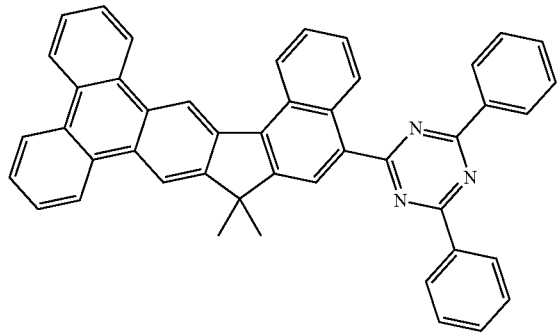
EX39
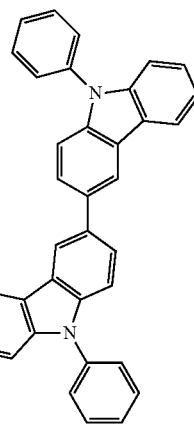
A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature(about 25° C.) and under atmospheric pressure.

Example 6

Figure 2:
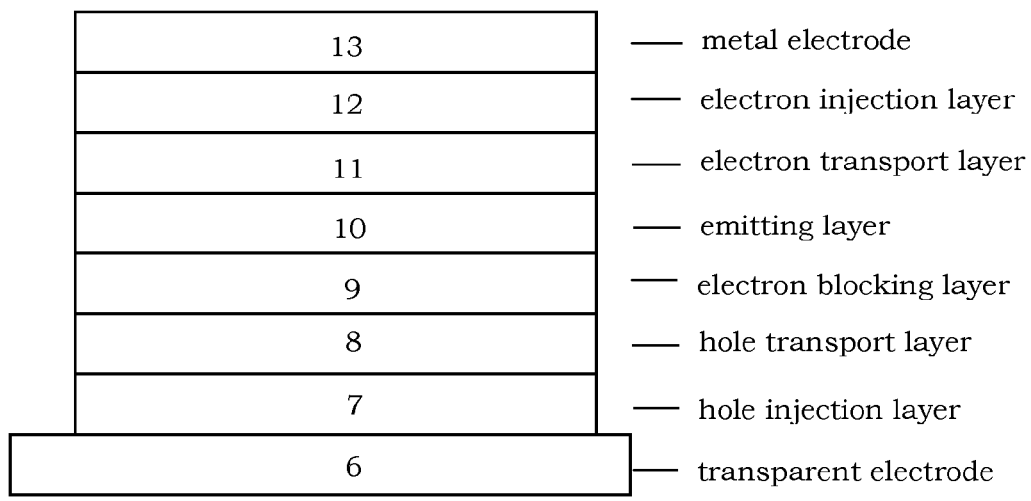
FIG. 2 show one example of organic EL device in the present invention. 6 is transparent electrode, 13 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is electron transport layer which is deposited onto 10, 12 is electron injection layer which is deposited on to 11.

Using a procedure analogous to the above mentioned general method, fluorescent blue-emitting organic EL device having the following device structure was produced(See FIG. 2): ITO/HAT-CN(10 nm)/NPB(800 nm)/electron blocking material(EBM)(5 nm)/blue host doped 5% dopant (30 nm)/ET1 co-deposit 5% Li(35 nm)/Al(160 nm). The I-V-B(at 1000 nits) and half-life time of fluorescent blue-emitting organic EL device testing report as Table 1, The half-life time is defined that the initial luminance of 1000 $cd/m^2$ has dropped to half.

TABLE 1

| EBM | Blue host | Dopant | Voltage (V) | Efficiency (cd/A) | CIE(y) | Half-life time (hour) |
|---|---|---|---|---|---|---|
| EB2 | PT-312 | D1 | 5.0 | 5.0 | 0.176 | 240 |
| EB2 | EX1 | D1 | 4.8 | 5.6 | 0.178 | 310 |
| EB2 | EX1 | EX13 | 4.5 | 4.0 | 0.143 | 120 |
| EX23 | PT-312 | D1 | 5.2 | 5.2 | 0.181 | 380 |
| EX23 | EX1 | D1 | 5.0 | 5.6 | 0.180 | 360 |
| — | EX1 | D1 | 4.8 | 5.4 | 0.182 | 150 |

Example 7

Using a procedure analogous to the above mentioned general method, fluorescent blue-emitting organic EL device having the following device structure was produced(See FIG. 1): ITO/HAT-CN(10 nm)/NPB(800 nm)/PT-312 doped 5% D1(30 nm)/hole blocking material(HBM)(5 nm)/electron transport material(ETM) co-deposit 5% Li/Al(160 nm). The I-V-B(at 1000 nits) and half-life time of fluorescent blue-emitting organic EL device testing report as Table 2, The half-life time is defined that the initial luminance of 1000 $cd/m^2$ has dropped to half.

TABLE 2

| ETM | HBM | Voltage (V) | Efficiency [cd/A] | CIE(y) | Half-life time (hour) |
|---|---|---|---|---|---|
| ET1 | ET2 | 4.5 | 5.5 | 0.175 | 250 |
| ET1 | EX30 | 4.5 | 5.6 | 0.176 | 290 |
| EX26 | ET2 | 4.7 | 5.8 | 0.178 | 280 |
| EX26 | — | 5.0 | 5.1 | 0.183 | 160 |

Example 8

Figure 3:
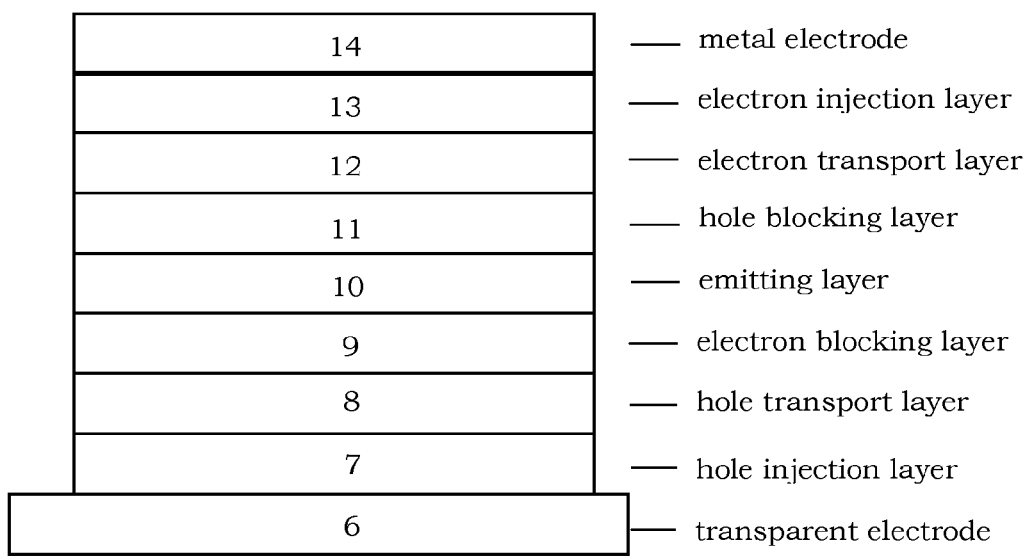
FIG. 3 show one example of organic EL device in the present invention. 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited onto 11, 13 is electron injection layer which is deposited on to 12.

Using a procedure analogous to the above mentioned general method, phosphorescent emitting organic EL device having the following device structures are produced(See FIG. 3.):ITO/HAT-CN(10 nm)/NPB(800 nm)/EBM(5 nm)/phosphorescent host(PHhost)+15% D2 (30 nm)/HBM(10 nm)/ET2 co-deposit 50% LiQ(35 nm)/LiQ(5 nm)/Al(160 nm). The I-V-B(at1000 nits) and half-life time of phosphorescent emitting organic EL device testing report as Table 3. The half-life time is defined that the initial luminance of 3000 $cd/m^2$ has dropped to half.

TABLE 3

| PHhost | HBM | Voltage (V) | Efficiency (cd/A) | CIE(x,y) | Half-life time (hour) |
|---|---|---|---|---|---|
| BAlq | ET2 | 5.8 | 29 | 0.45,0.56 | 300 |
| EX39 | ET2 | 4.3 | 36 | 0.43,0.59 | 550 |
| EX39 | EX30 | 3.8 | 35 | 0.43,0.59 | 580 |
| EX39 | — | 4.0 | 32 | 0.43,0.59 | 450 |

In the above preferred embodiments for organic EL device test report(see Table 1 to Table 3), we shown that the material with a general formula(A) used as emitting host or dopant, hole blocking layer(HBL), electron blocking layer (EBL), electron transport layer(ETL) and hole transport layer(HTL) in the present invention display good performance than the prior art of OLED materials.

To sum up, the present invention discloses a material which can be used for organic EL device is disclosed. More specifically, an organic EL device employing the material as emitting host or dopant, hole blocking layer(HBL), electron blocking layer(EBL), electron transport layer(ETL) and hole transport layer(HTL).The mentioned the material are represented by the following formula(A):

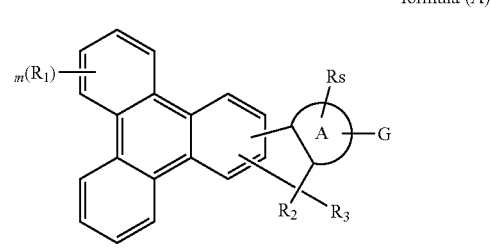

formula (A)

wherein A represents a substituted or unsubstituted fused ring hydrocarbon units with two to three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $R_s$ represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A material with a general formula(A) as follows:

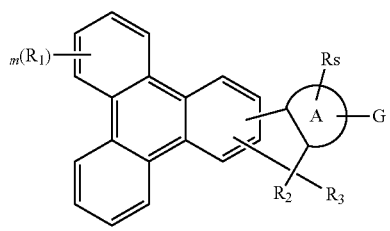

formula (A)

wherein A represents a substituted or unsubstituted fused ring hydrocarbon units with two to three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The material according to claim 1, wherein the G is represented by the following formulas:

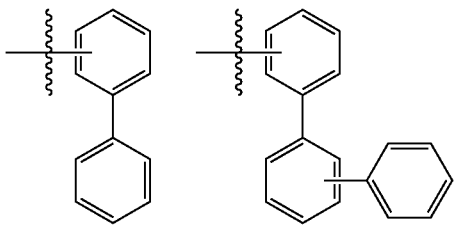

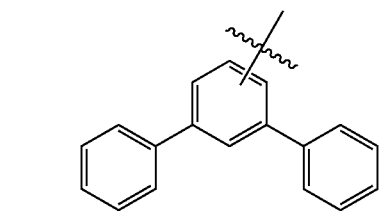

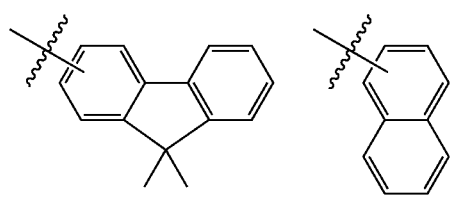

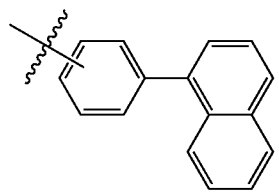

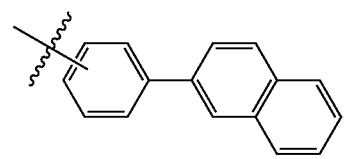

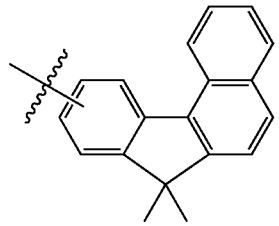

-continued
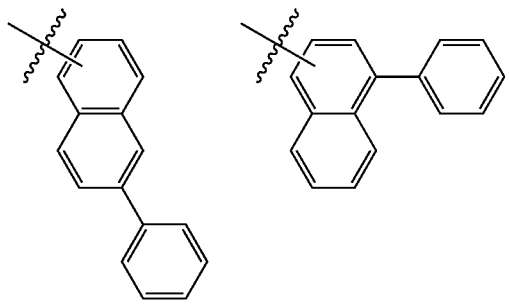
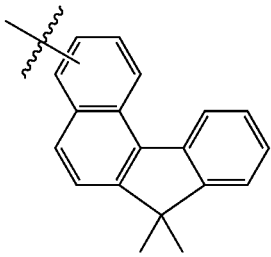
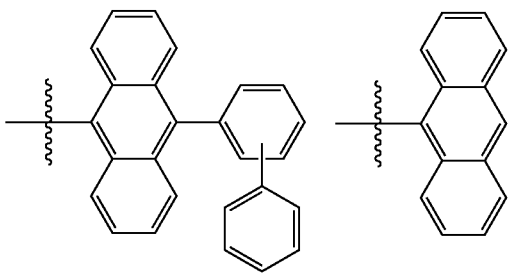
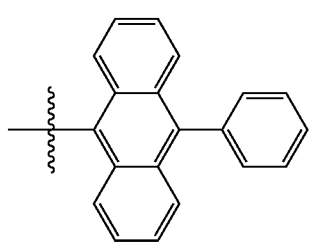
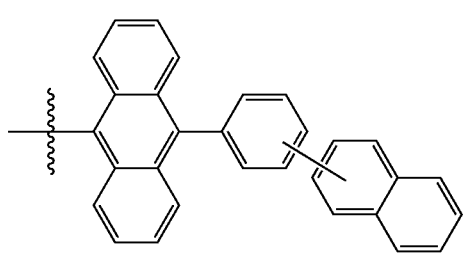
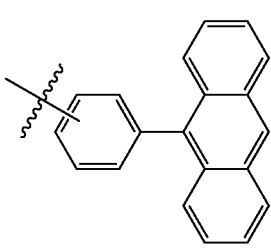
-continued
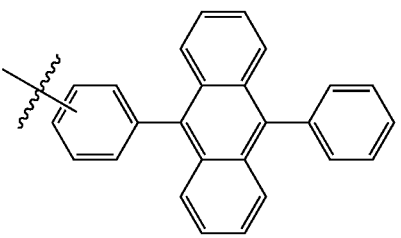
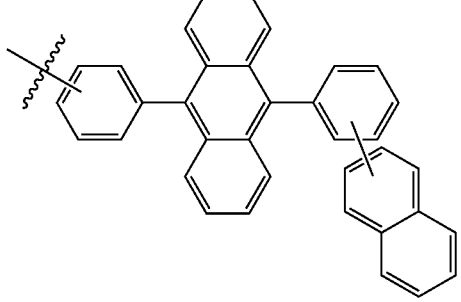
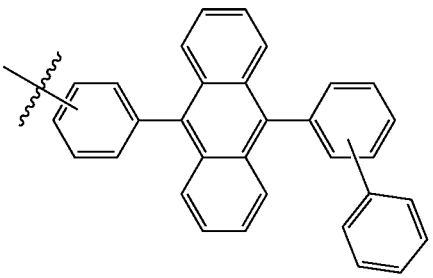
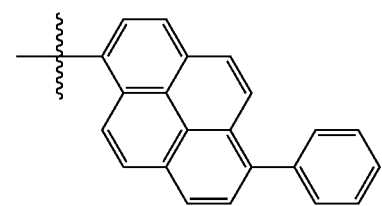
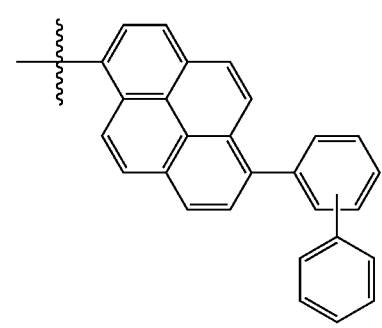
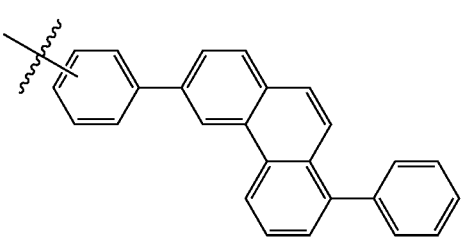

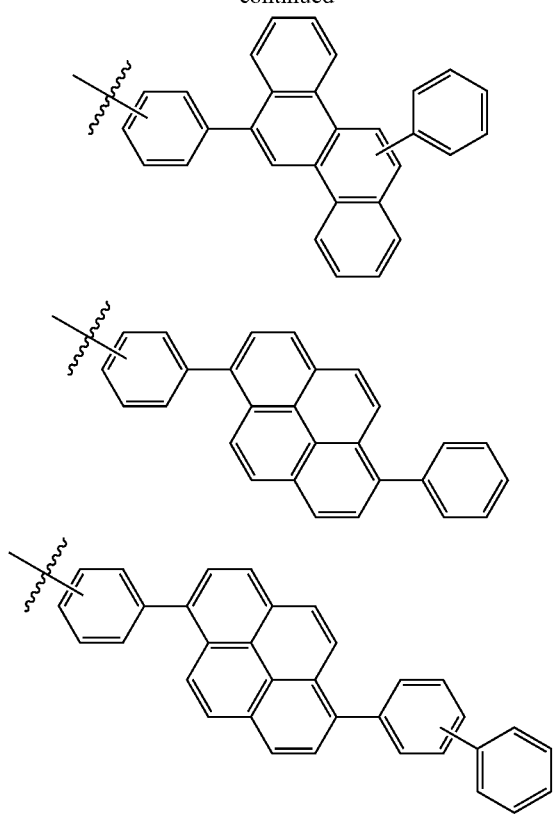
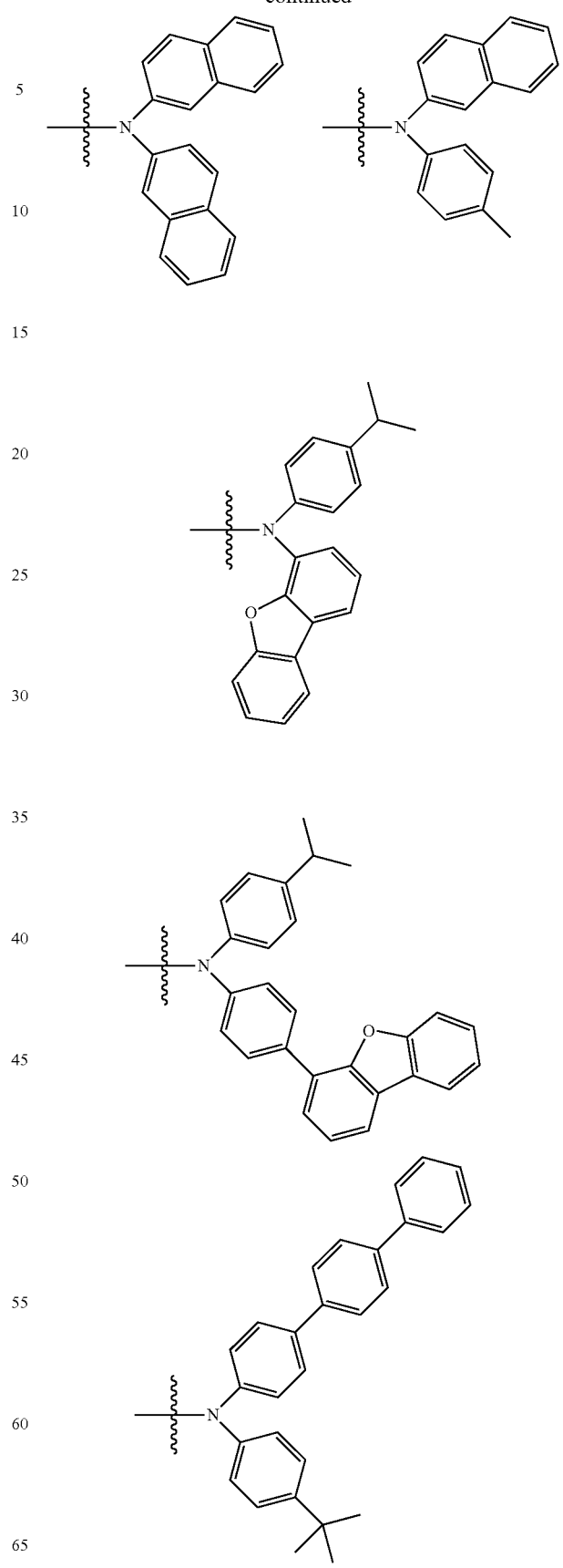

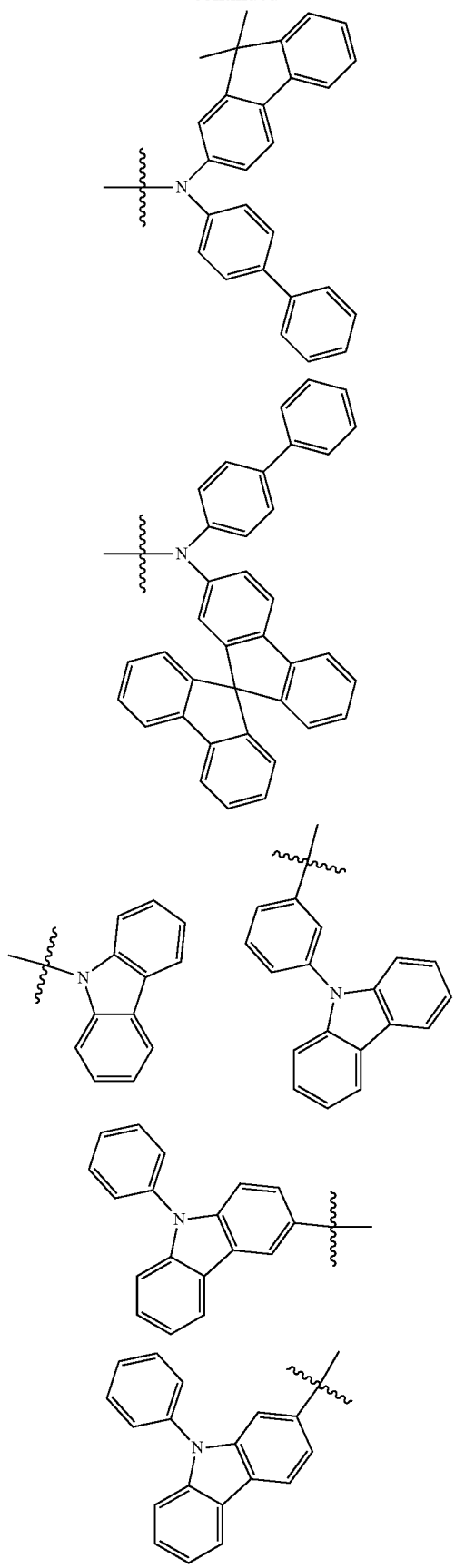
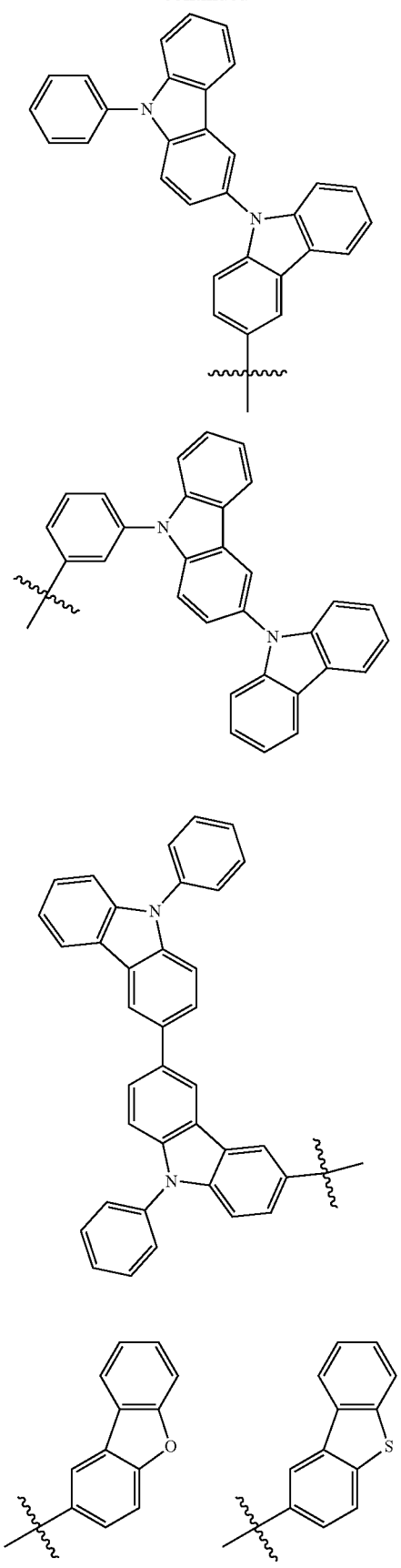

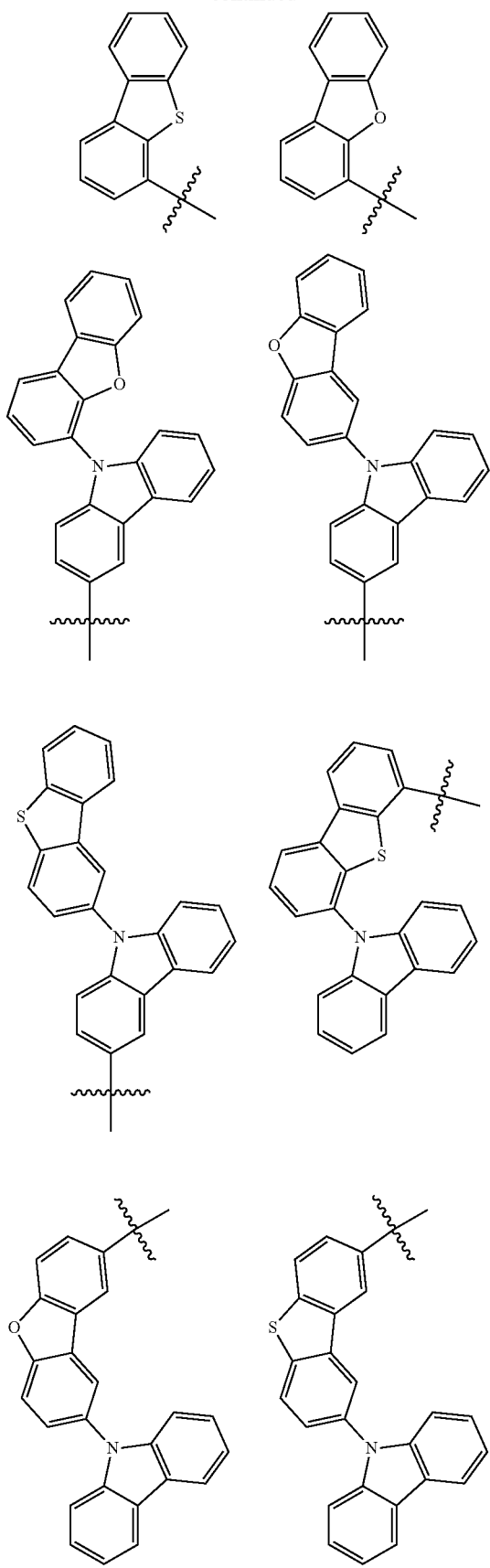
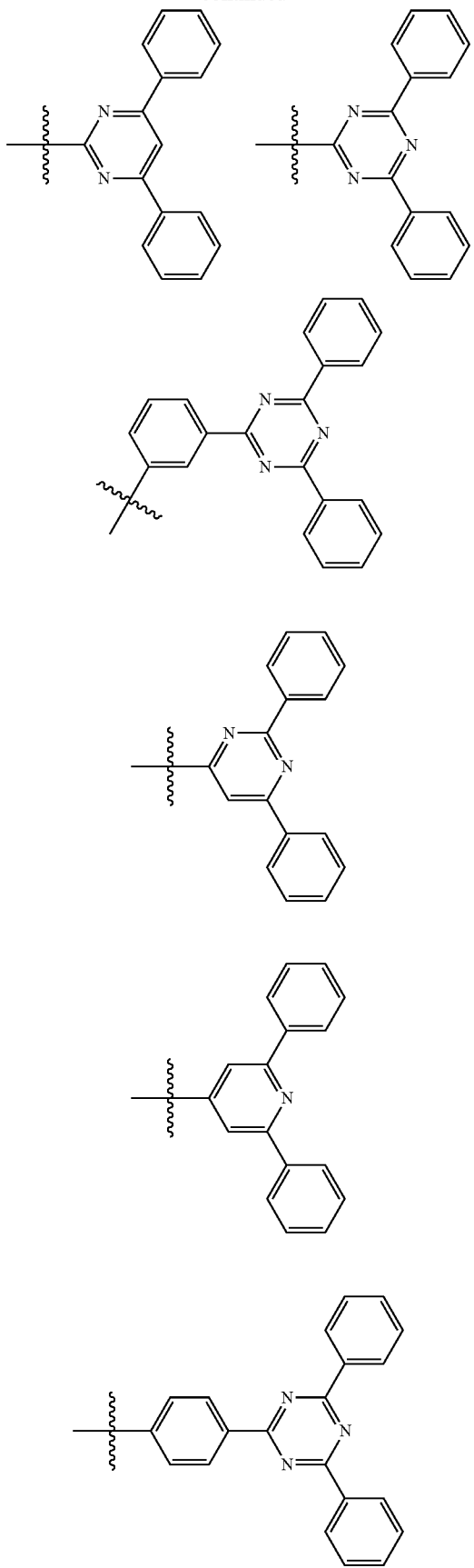

-continued
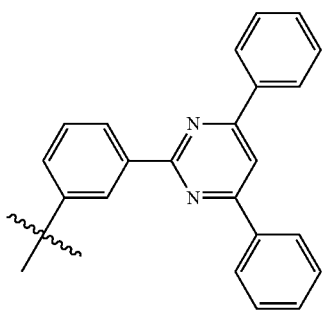
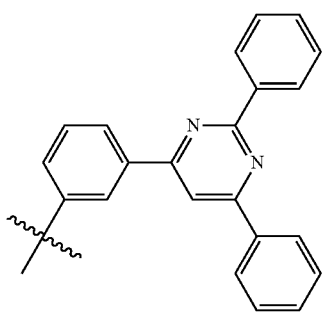
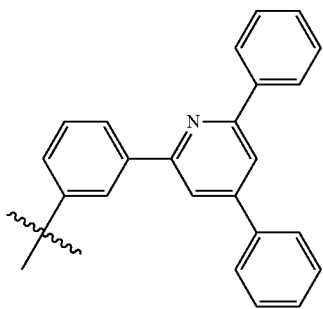
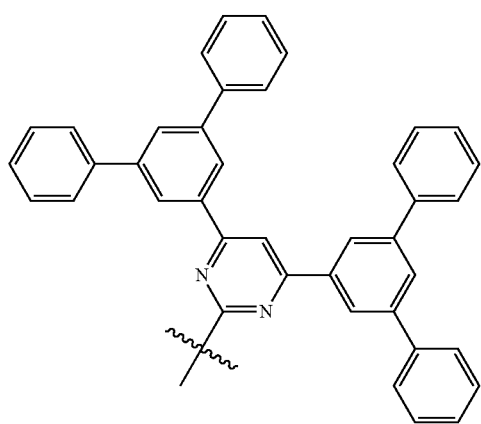
-continued
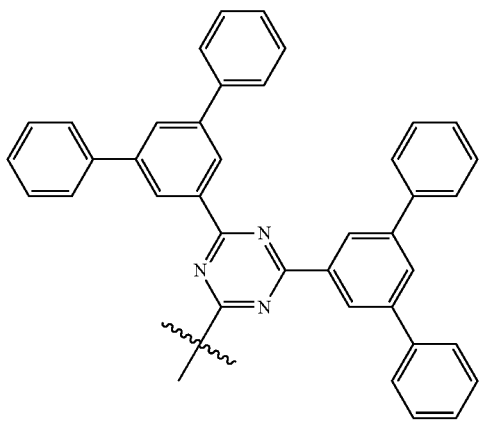
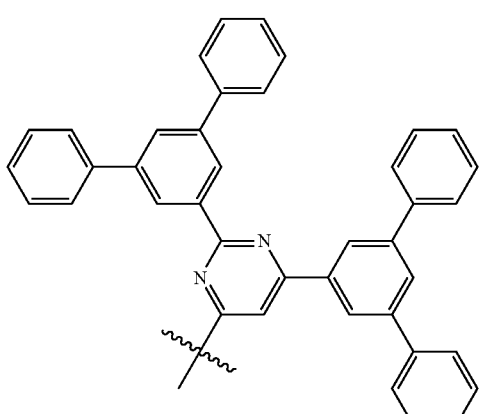
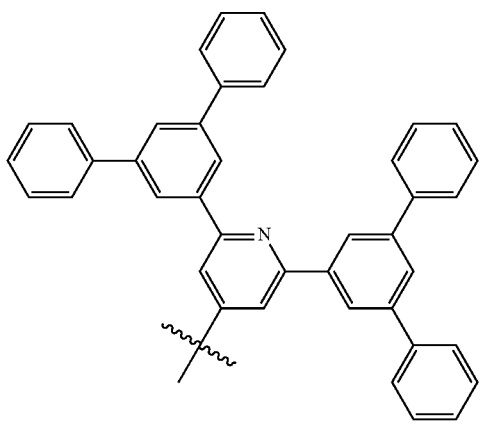

-continued
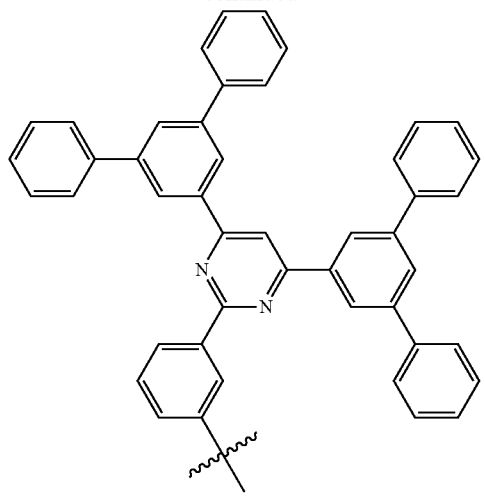
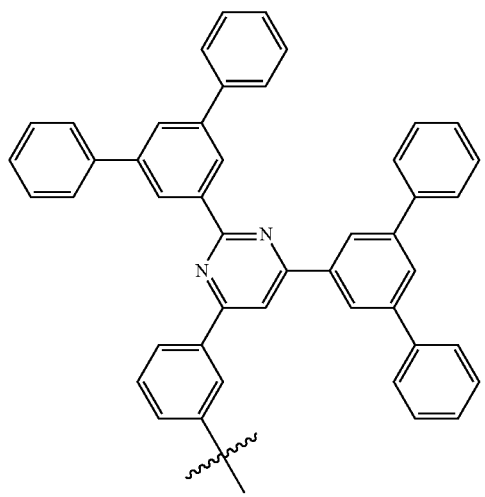
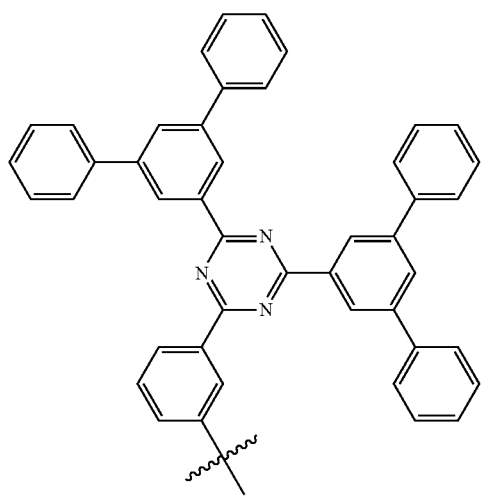
-continued
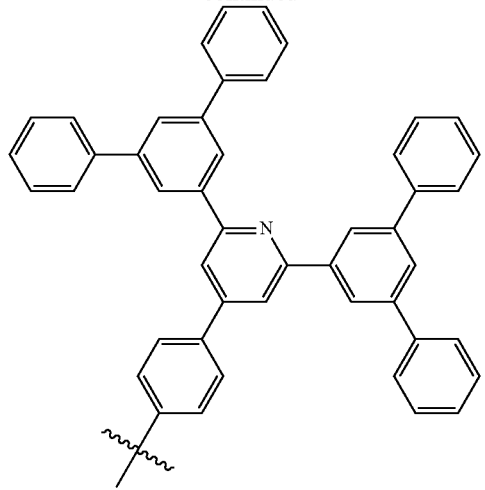
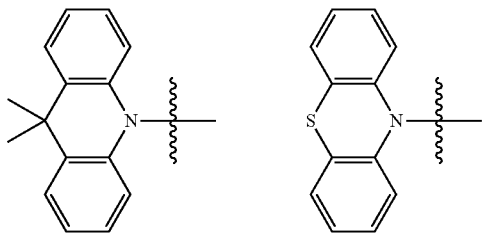
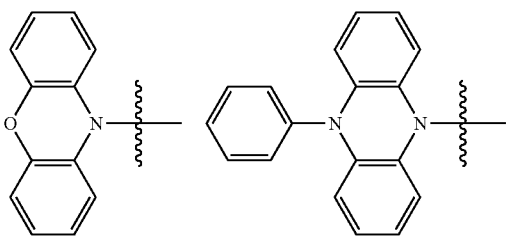
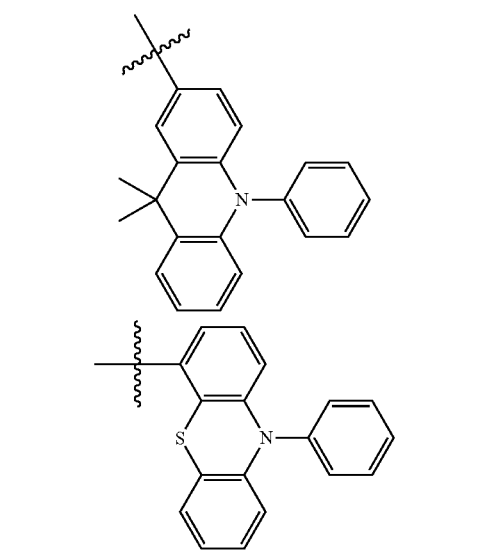

-continued
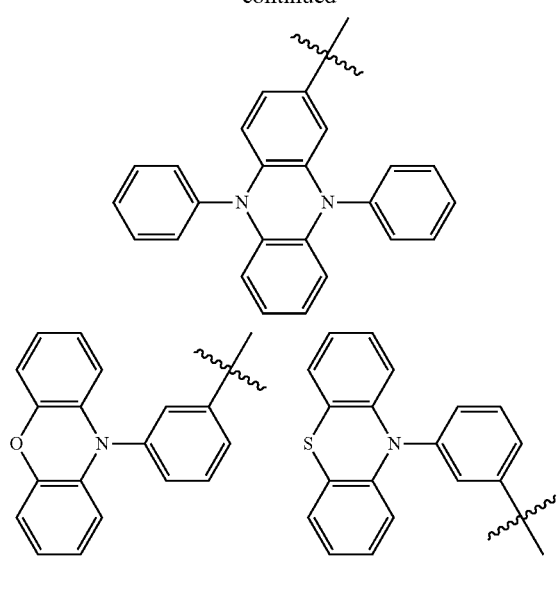
3. The material according to claim 1, wherein the material are represented by the following formula(1) to formula(9):
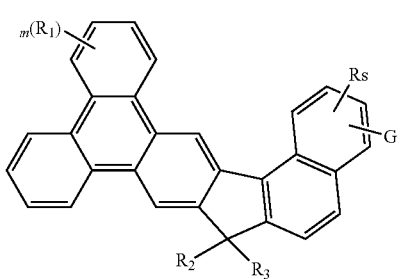
formula(1)
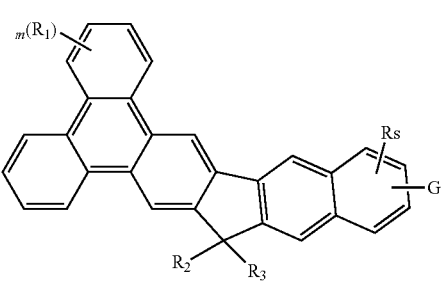
formula(2)
-continued
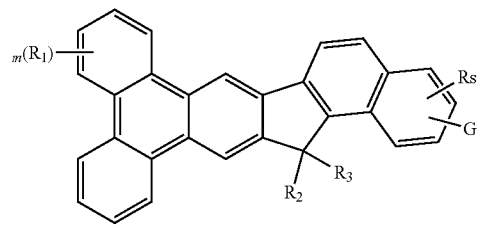
formula(3)
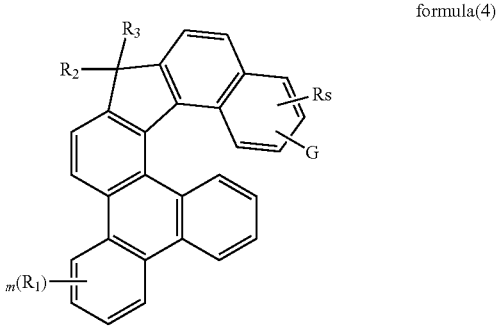
formula(4)
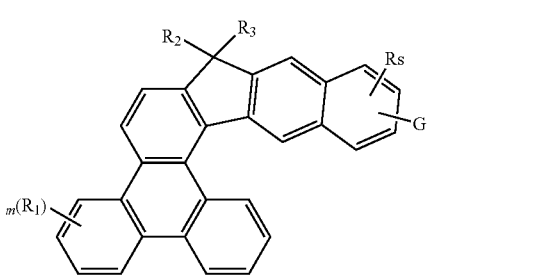
formula(5)
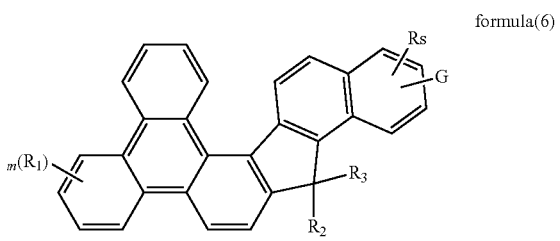
formula(6)
formula(7)
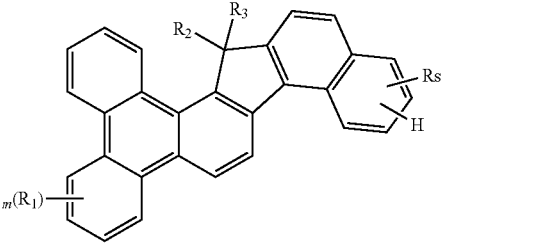
formula(7)
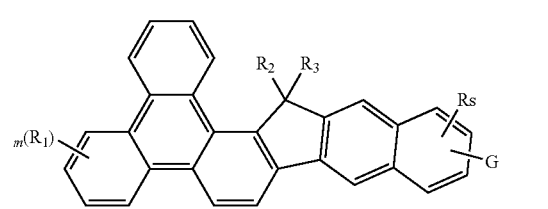
formula(8)

formula(9)

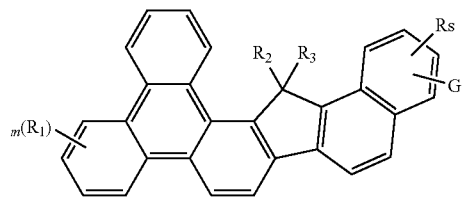

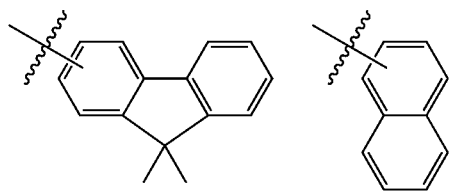

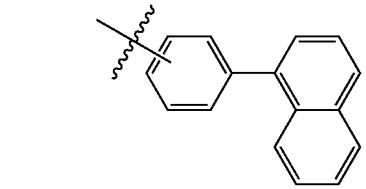

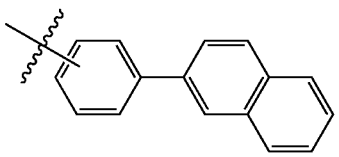

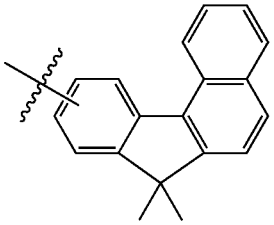

Wherein m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that the G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

4. The material according to claim 3, wherein the G is represented by the following formulas:

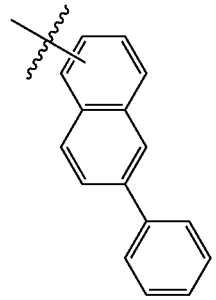

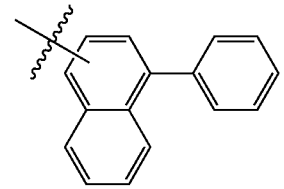

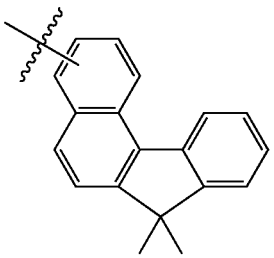

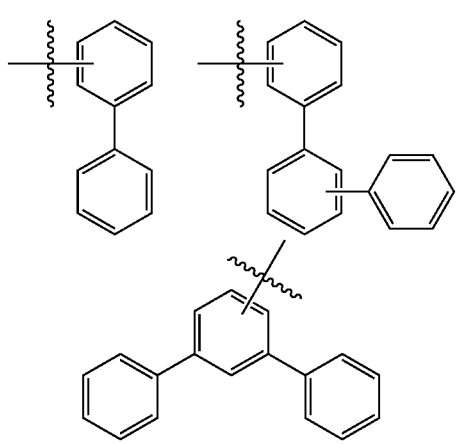

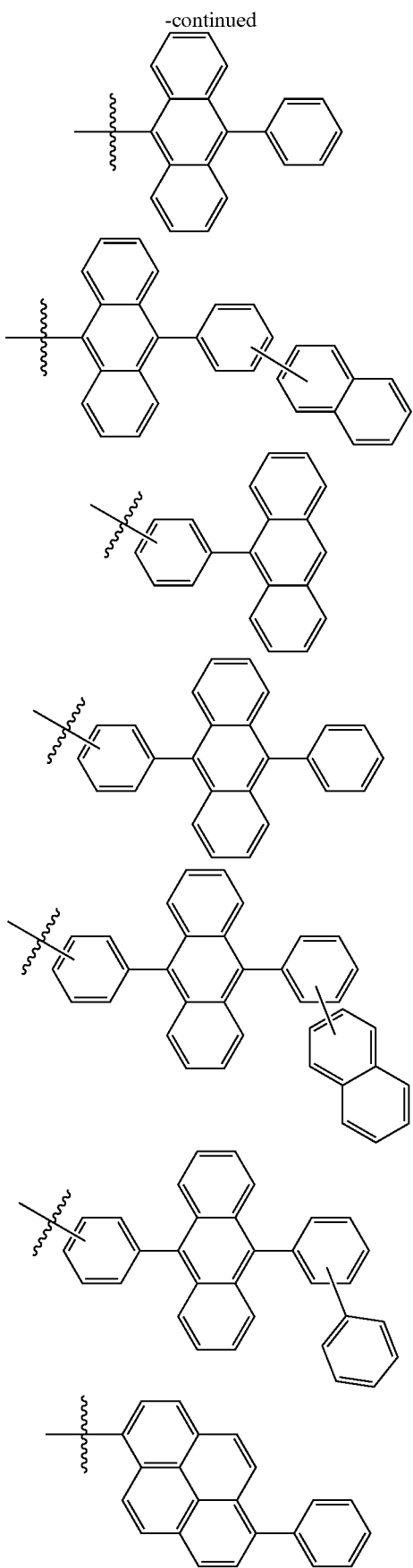

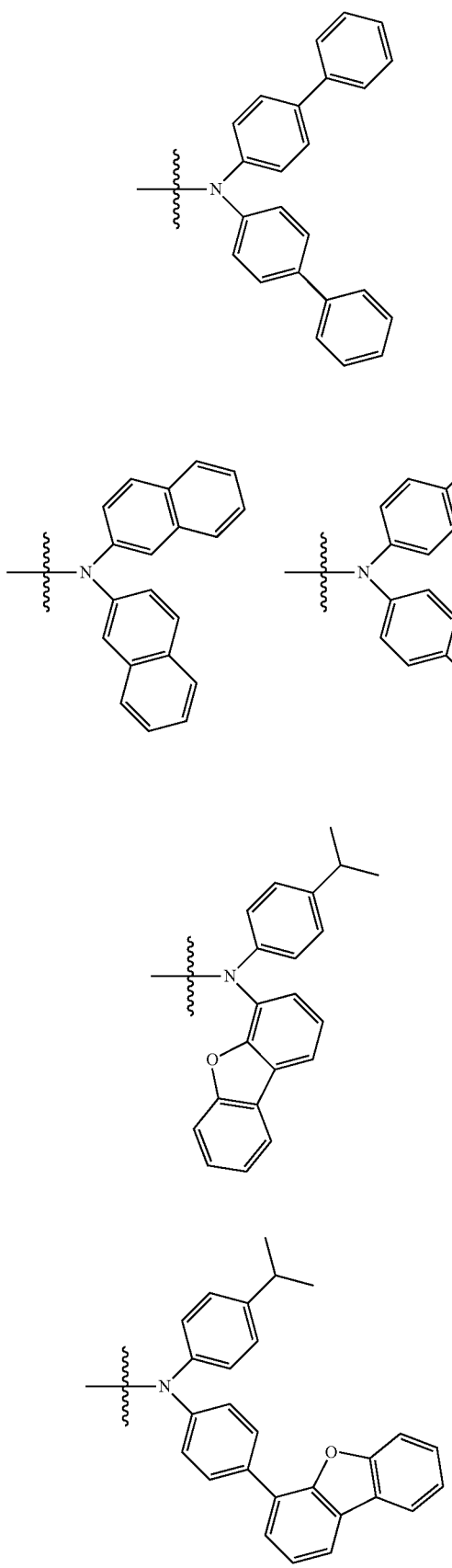
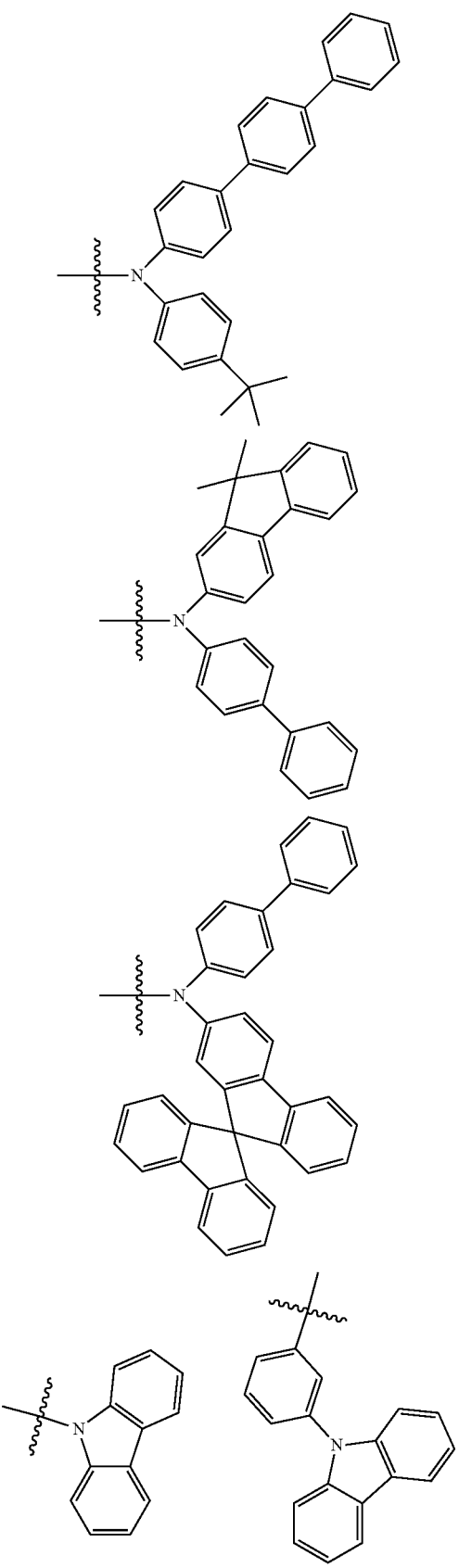

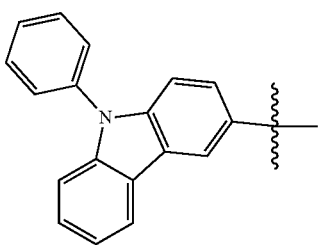
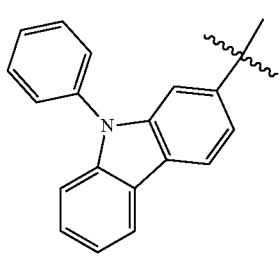
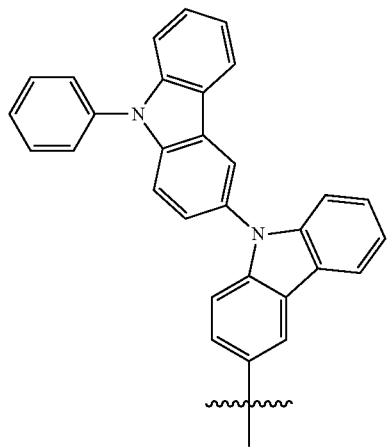
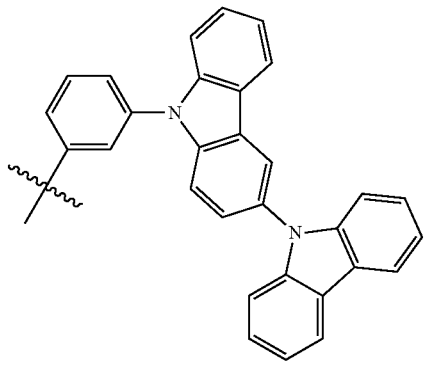
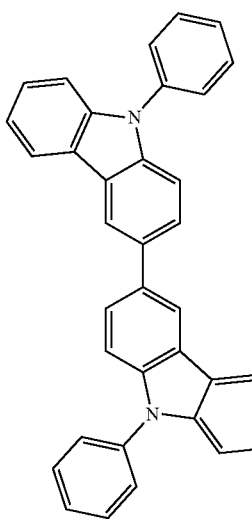
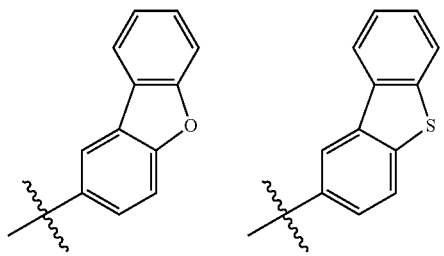
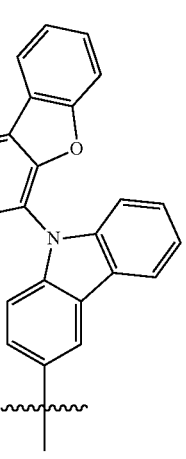
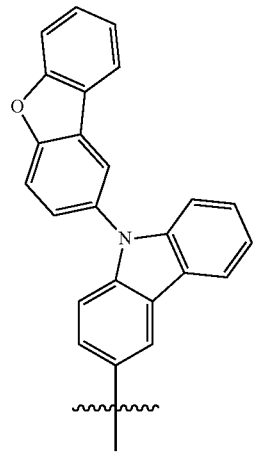

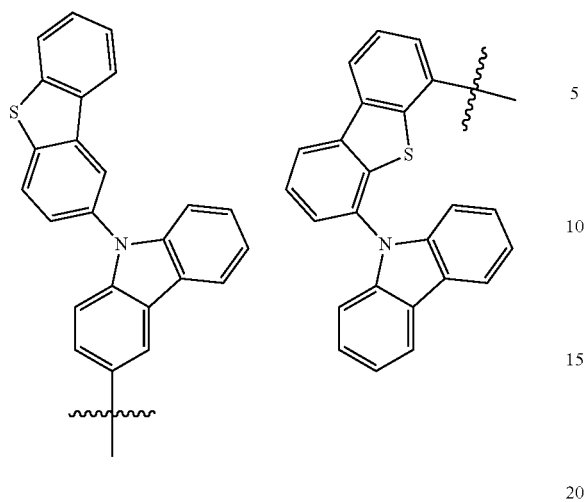
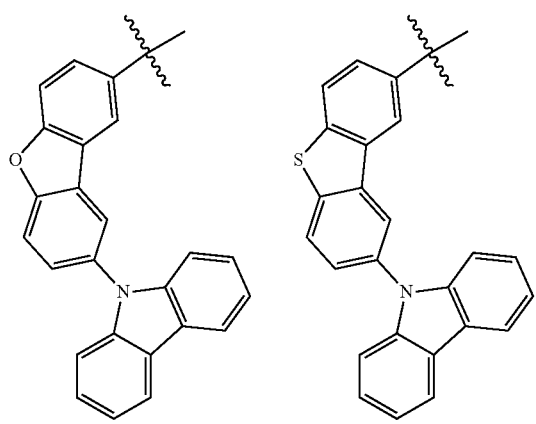
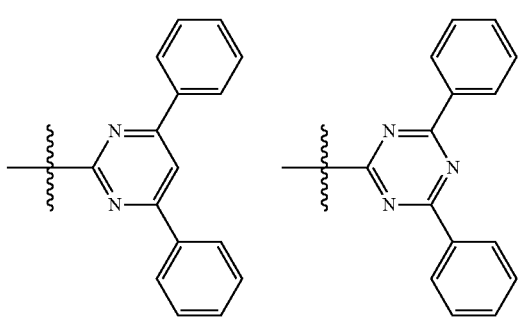
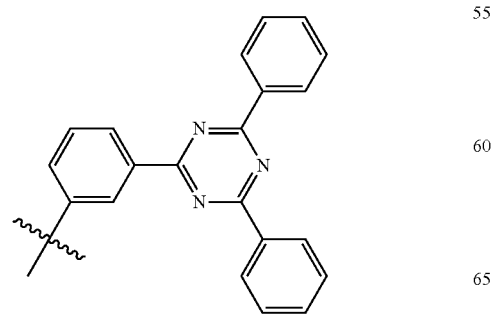
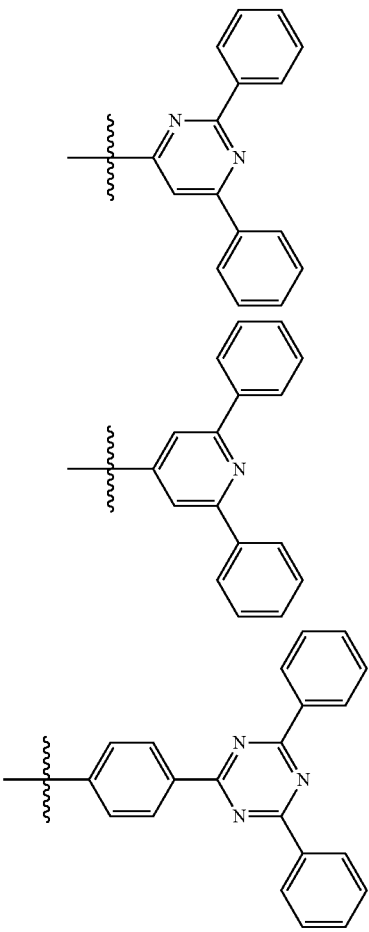
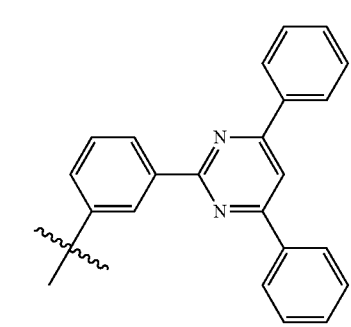
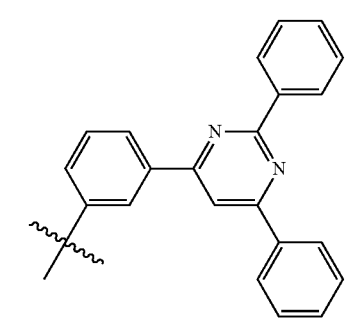

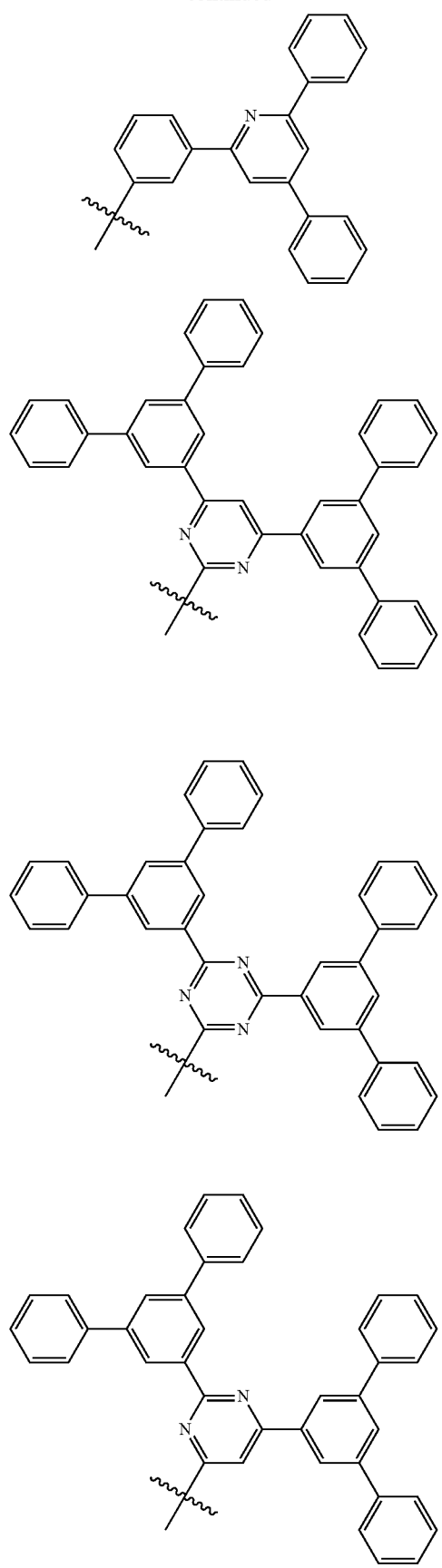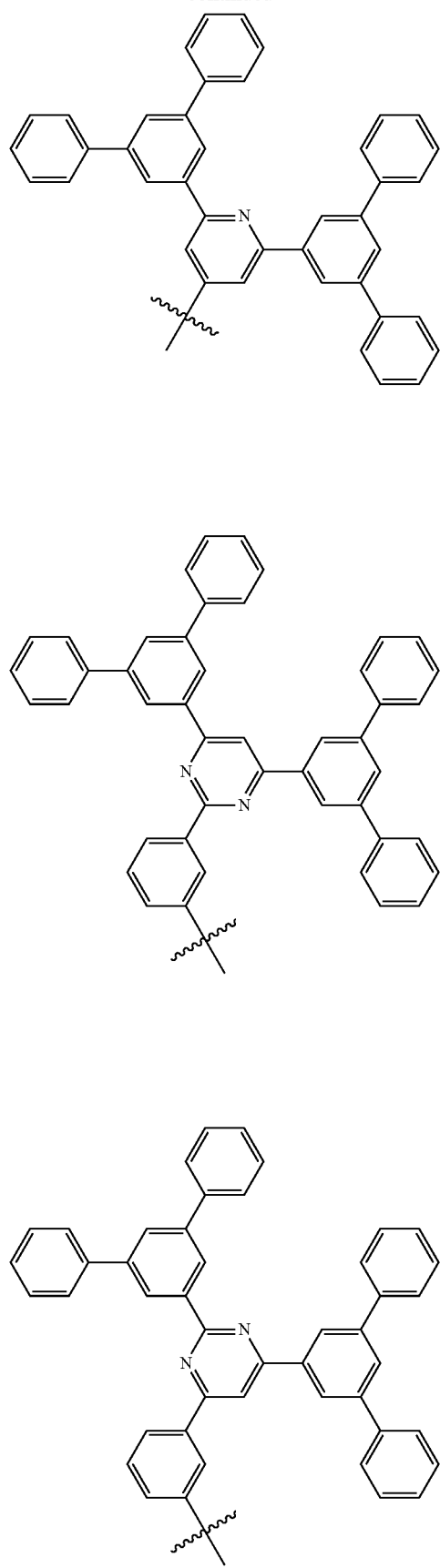

99
-continued

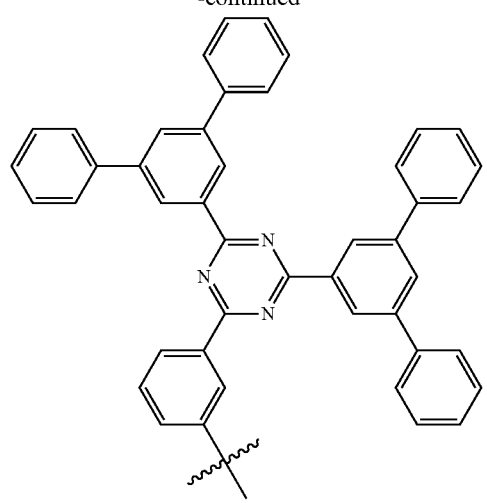

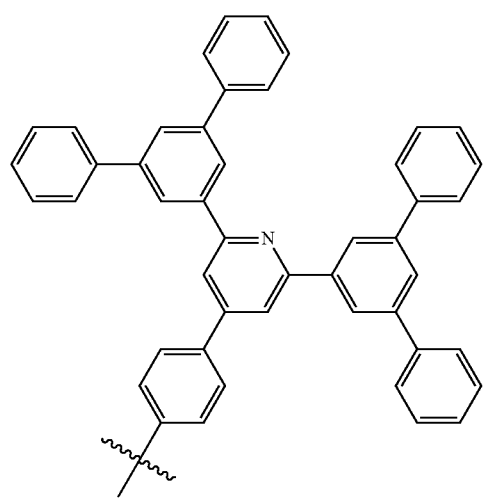

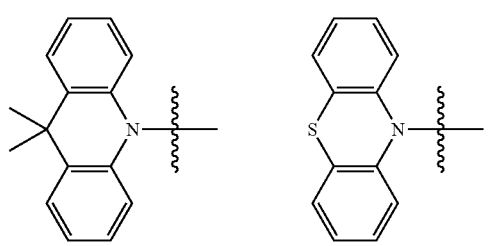

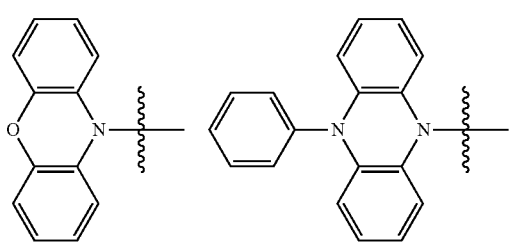

100
-continued

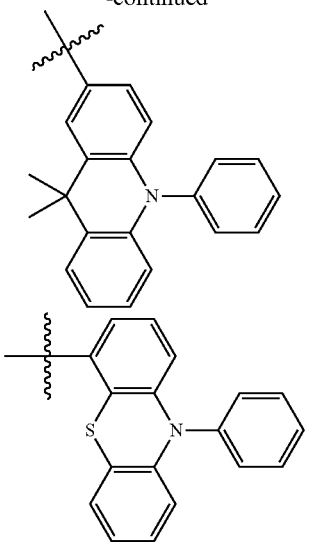

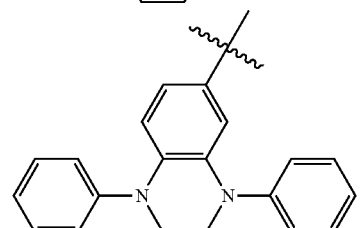

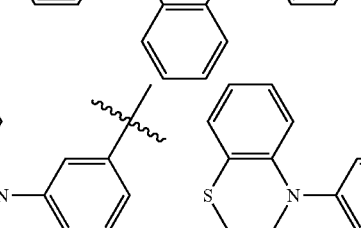

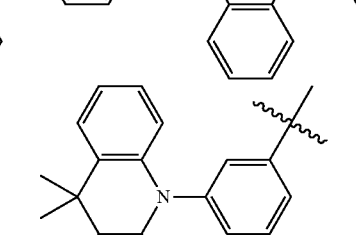

5. A organic electroluminescence device comprising a pair of electrodes consisting of a cathode and an anode, and between the pairs of electrodes comprising at least a light emitting layer, one or more layers of organic thin film layer, wherein the light emitting layer or the organic thin film layer comprising the material according to claim 1.

6. The organic electroluminescence device according to claim 5, wherein the light emitting layer comprising the material with a general formula(A) is a host material.

7. The organic electroluminescence device according to claim 5, wherein the light emitting layer comprising the material with a general formula(A) is a fluorescent dopant material.

8. The organic electroluminescence device according to claim 5, wherein the light emitting layer comprising the material with a general formula(A) is a thermally activated delayed fluorescence host material.

9. The organic electroluminescence device according to claim 5, wherein the light emitting layer comprising the material with a general formula(A) is a thermally activated delayed fluorescence dopant material.

10. The organic electroluminescence device according to claim 5, wherein the organic thin film layer comprising the material with a general formula(A) is a hole blocking material.

11. The organic electroluminescence device according to claim 5, wherein the organic thin film layer comprising the material with a general formula(A) is a electron blocking material.

12. The organic electroluminescence device according to claim 5, wherein the organic thin film layer comprising the material with a general formula(A) is a hole transport material.

13. The organic electroluminescence device according to claim 5, wherein the organic thin film layer comprising the material with a general formula(A) is a electron transport material.

14. The organic electroluminescence device according to claim 5, wherein the light emitting layer emits phosphorescent red, blue, green and yellow lights.

15. The organic electroluminescence device according to claim 5, wherein the light emitting layer emits thermally activated delayed fluorescent red, blue, green and yellow lights.

16. The organic electroluminescence device according to claim 5, wherein the device is an organic light emitting device.

17. The organic electroluminescent device according to claim 5, wherein the device is a lighting panel.

18. The organic electroluminescent device according to claim 5, wherein the device is a backlight panel.

* * * * *